(12) United States Patent
Lee et al.

(10) Patent No.: US 7,893,104 B2
(45) Date of Patent: Feb. 22, 2011

(54) PROCESS FOR SYNTHESIZING SILVER-SILICA PARTICLES AND APPLICATIONS

(76) Inventors: Jong-Min Lee, 301-102, Kum Hwa Apt, Sanggai-dong, Yongin Si Giheung-gu (KR); Dae-Wook Kim, 1022 SE. 163$^{rd}$ St., Hawthorne, FL (US) 32640; Young-Doo Jun, Itep, 8-13 Kotech Blgd. 503, Teheran-Ro, Gangnam-Gu (KR) 135080; Seong-Guen Oh, 1022 SE. 163$^{rd}$ St., Hawthorne, FL (US) 32640

( * ) Notice: Subject to any disclaimer, the term of this patent is extended or adjusted under 35 U.S.C. 154(b) by 427 days.

(21) Appl. No.: 12/041,372

(22) Filed: Mar. 3, 2008
(Under 37 CFR 1.47)

(65) Prior Publication Data
US 2009/0149426 A1 Jun. 11, 2009

Related U.S. Application Data

(60) Provisional application No. 60/892,499, filed on Mar. 1, 2007.

(51) Int. Cl.
*A61K 31/28* (2006.01)
*A61K 31/695* (2006.01)
*A61K 47/00* (2006.01)

(52) U.S. Cl. .......... 514/495; 514/63; 514/492; 514/772.1

(58) Field of Classification Search .......... 514/63, 514/492, 495, 772.1
See application file for complete search history.

(56) References Cited

FOREIGN PATENT DOCUMENTS

| KR | 10-2004-0039256 | 5/2004 |
|----|-----------------|--------|
| KR | 10-2004-0052636 | 6/2004 |
| KR | 10-2004-0096456 | 11/2004 |
| KR | 1-1-2006-5012094 | 5/2005 |

OTHER PUBLICATIONS

S.J. Oldenburg et al., Nanoengineering of optical resonances, Chemical Physics Letters 288 (1988) pp. 243-247.
Wei Wang et al., Photochemical Incorporation of Silver Quantum Dots in Monodisperse Silica Colloids for Photonic Crystal Applications, J.Am Chem. Soc. 2001, 123 pp. 12528-12535.
Ashavani Kumar et al., Silver-nanoparticle-embedded antimicrobial paints based on vegtable oil, Nature Materials 7, .236-241 (2008).
Jong-Min Lee et al., New Approach for Preparation of Silver-polystyrene Heterogeneous Nanocomposite by Polyol Process, Chemistry Letters, copyright 2005 The Chemical Society of Japan.
Chun-Wei Chen et al. Preparation of Platinum Colloids on Polystyrene Nanospheres and Their Catalytic Properties in Hydrogenation, Chem. Mater. 1999, 11 pp. 1381-1389.
Darren Lawless et al., Reduction and Aggregation of Silver Ions at the Surface of Colloidal Silica, J. Phys. chem. 1994, 98, pp. 9619-9625.
Zhong-Jie Jiang et al., Seed-Mediated Growth Technique for the Preparation of a Silver Nanoshell on a silica Sphere, J. Phys. Chem. B 2003, 107, pp. 12411-12415.
V. G. Pol et al., Deposition of Gold Nanoparticles on Silica Spheres: A Sonochemical Approach, Chem. Mater. 2003,15, pp. 1111-1118.
J. Zhang et al. Facile Methods to Coat Polystyrene and Silica Colloids with Metal, abstract only.
Shuming Nie et al., Probing Single Molecules and Single Nanoparticles by Surface-Enhanced Raman Scattering, Abstract only.
Zhenlin Wang et al., Three-dimensional self-assembly of metal nanoparticles: Possible photonic crystal with a complete gap below the plasma frequency, Physical Review B, vol. 64, 113108.
S.A. Kalele at al., Optical detection of antibody using silica-silver core-shell particles, abstract only.
F. Fievet et al., Homogeneous and heterogeneous nucleations in the polyol process for the preparation of micron and submicron size metal particles, abstract only.
Pierre-Yves Silvert et al., Preparation of colloidal silver dispersions by the polyol process, J. Mater. Chem., 1997, 7, pp. 293-299.

(Continued)

*Primary Examiner*—Raymond J Henley, III
(74) *Attorney, Agent, or Firm*—Christopher Paradies; Fowler White Boggs P.A.

(57) ABSTRACT

Size-controlled immobilization of metal nano-clusters onto particles or nanoparticles is achieved using a polyol process. Polyol processing makes it possible to use thiol groups as a chemical protocol to functionalize the surface of particles, such as silica and polystyrene nanoparticles. Metal nano-clusters, such as silver, gold, platinum and palladium, nucleate and grow on the surface of the particles. The metal nano-clusters may be synthesized in a one-pot process from metal salts, nitrates, nitrites, sulfates, sulfites and the like. Any source of metal ions compatible with the polyol suspension and selected particles may be used. The size of immobilized metal nano-clusters may be controlled by additions of a poly (vinylpyrrolidone) or other polymer capable of regulating the metal ion reduction and nucleation process and by controlling concentration of metal ions, the nucleation and/or growth temperatures, and processing time.

24 Claims, 10 Drawing Sheets

OTHER PUBLICATIONS

Pierre-Yves Silvert et al., Preparation of colloidal silver dispersions by the polyol process. Part 1-Synthesis and characterization, J. Mater. Chem., 1996, 6, 573-577, abstract only.

Yoshio Kabayashi et al., Deposition of gold nanoparticles on silica spheres by electroless metal plating technique, abstract only.

Ashavani Kumar et al., Silver Nanoparticles Embedded Anti-microbial Paints Based on Vegteble Oil, copyright 2008 Nature Publishing Group, 8 pages.

PROCESS FOR SYNTHESIZING SILVER-SILICA PARTICLES AND APPLICATIONS

REFERENCE TO RELATED APPLICATION

This application claims the benefit of the filing date of U.S. Provisional Patent Application No. 60/892,499 filed Mar. 1, 2007, the description and figures of which are hereby incorporated by reference in its entirety.

BACKGROUND OF THE INVENTION

D. Lawless, S. Kapoor, P. Kennepohl, D. Meisel and N. Serpone, *J. Phys. Chem.* 98 (1994), p. 9619; S. J. Oldenburg, R. D. Averitt, S. L. Westcott and N. J. Halas, *Chem. Phys. Lett.* 288 (1998), p. 243; Z. J. Jiang and C. Y. Liu, *J. Phys. Chem. B* 107 (2003), p. 12411; W. Wang and S. A. Asher, *J. Am. Chem. Soc.* 123 (2001), p. 12528; and D. Wang, V. Salgueiriño-Maceira, L. M. Liz-Marzán and F. Caruso, *Adv. Mater.* 14 (2002), p. 908 disclose methods by which metal nanoparticles are deposited to various inorganic supports. While these methods make it easy to handle metal nanoparticles and reduce metal nanoparticle agglomeration, the methods are very complex and are extremely difficult to control for repeatedly producing composite particles in a controlled and narrow nano-size.

Alternative routes for producing small composite particles have been suggested by others as a way to simplify the very complex reactions and control processes required by previously known processes of synthesizing such metal-inorganic composite particles. One method is sono-chemical deposition, as disclosed by V. G. Pol, A. Gedanken and J. Calderon-Moreno, *Chem. Mater.* 15 (2003), p. 1111. Another method is electroless plating, as disclosed by Y. Kobayashi, Y. Tadaki, D. Nagao and M. Konno, *J Colloid Interface Sci.* 283 (2005), p. 601. Yet another method is electrostatic attraction techniques, as disclosed by J. Zhang, J. Liu, S. Wang, P. Zhan, Z. Wang and N. Ming, *Adv. Funct. Mater.* 14 (2004), p. 1089. However, these processes are still difficult to control, expensive, and/or not commercially scalable for mass production of nano-sized metal composite particles, which may be a desired range of size in order to dramatically improve catalyst efficiency and performance in commercial use of such composite particles.

Composite nano-sized particles have potential applications in various fields, such as surface-enhanced Raman scattering (SERS), as disclosed in S. Nie and S. R. Emory, *Science* 275 (1997), p. 1102, photonic crystals, as disclosed in Z. L. Wang, C. T. Chan, W. Y. Zhang, Z. Chen, N. B. Ming and P. Sheng, *Phys. Rev. B* 64 (2001), p. 113108, catalysis, as disclosed in C. W. Chen, T. Serizawa and M. Akashi, *Chem. Mater.* 11 (1999), p. 1381, and biochemistry for chemical sensors, as disclosed in S. A. Kalele, S. S. Ashtaputre, N. Y. Hebalkar, S. W. Gosavi, D. N. Deobagkar, D. D. Deobagkar and S. K. Kulkarni, *Chem. Phys. Lett.* 404 (2005), p. 136.

A polystyrene-metal nanocomposite particle was first disclosed in J. M. Lee, D. W. Kim, Y. H. Lee and S. G. Oh, *Chem. Lett.* 34 (2005) (7), p. 928. However, this process used already formed polystyrene spheres and deposited metal onto the surface of the spheres using a polyol process. The polyol process is a chemical reduction method using polyol, such as ethylene glycol and diethylene glycol, to chemically reduce a metal salt. In this process, polyol acts both as the solvent of the metallic precursor and as the reducing agent, such as disclosed in F. Fievet, J. P. Lagier, B. Blin, B. Beaudoin and M. Figlarz, *Solid State Ionics* 32/33 (1989), p. 198; P. Y. Silvert, R. Herrera-Urbina, N. Duvauchelle, V. Vijayakrishnan and K. Tekaia-Elhsissen, *J. Mater. Chem.* 6 (1996) (4), p. 573; and P. Y. Silvert, R. Herrera-Urbina and K. Tekaia-Elhsissen, *J. Mater. Chem.* 7 (1997) (2), p. 293. However, none of these references disclose any method of control that allows a one-pot process to produce nanoparticle clusters onto an inorganic particle surface, while controlling size of the composite and clusters.

Korean Patent Laid Open, entitled "Polymers and novel metals composites by alcohol reduction," which was filed Apr. 22, 2004 in the Korean Patent Office to Seong Geun Oh ("Oh Reference"), teaches a method for reduction of metals, such as platinum, palladium, gold, silver, osmium, iridium, ruthenium, and rodium or mixtures of any of these and other elemental metals, to obtain nano-sized metal particles as a colloid phase. The application is incorporated herein by reference in its entirety.

The polyol process is one type of alcohol reduction process. In this process, it is preferred to use an alcohol with a high boiling point to reduce metals not easily reduced at lower temperatures. Some examples of alcohols are listed, including ethylene glycol, diethylene glycol, trimethylene glycol, and isopropylene glycol. The Oh Reference teaches several examples of metal reduction processes for precious metals such as silver, platinum, palladium, and gold. However, this reference fails to teach any process capable of producing metal-particle complexes. Instead, the process is used merely to prepare metal colloids.

In another application laid open, Korean unexamined patent application no. 10-200400039256, entitled "Manufacturing method of silver-sulfur-silica complex nanoparticles having antibacterial, antifungal properties," which was published on May 10, 2004, particles were formed by binding silver ions on the surface of pre-existing 30-40 nanometer silica particles by adding the silica particles to a sulfur-containing functional additive, 3-mercaptopropyl trimethoxysilane, and using $NaBH_4$ or ascorbic acid as a reducing agent. The reference teaches the precipitation of the particles of 30-40 nm using ethanol, followed by a pulverization process. The 3-mercaptopropyl trimethoxysilane functionalizes the surface of the silica particles, and the $NaBH_4$ or ascorbic acid is used to reduce the silver ions from silver nitrate to elemental silver metal, which nucleates and grows on the functionalized surface of the silica particles. The resulting suspension includes silver-silica particle complexes; however, the suspension is unstable and is prone to gel at room temperature, requiring refrigeration during storage. Also, the process does not synthesize metal-particle complexes. Instead, it merely deposits metal nano-clusters on the surface of preexisting particles.

Recently, Kumar et al. have announced an in situ process for the formation of silver and gold nanoparticles in vegetable oil based paints using free radical reduction during the drying process. See Kumar et al., "Silver-nanoparticle-embedded antimicrobial paints based on vegetable oil," *Nature Materials*, vol. 7, March (2008). While a promising route for synthesis of low cost coating containing silver nanoparticles, the process changes the color of the paint to a dark yellow (silver nanoparticles) or reddish color (gold nanoparticles), which is a problem that must be addressed before this technology may be used as an external, decorative paint. Also, Kumar et al. suggests that a proportion of the silver present in the coatings is in an ionized form, which may lead to leaching of the ionic silver form the coating.

Herein, nano-sized, nano-clusters and nanoparticles refers to a mean size (i.e. hydraulic diameter, cross-section or thickness) no greater than 100 nanometers and no less than one nanometer, and only refers to nanoparticles that are formed in a bottom-up synthesis.

The sulfur-containing functional additive 3-mercaptopropyl trimethoxysilane (MPTS) is used in sol-gel processing. However, 3-mercaptopropyl triethoxysilane (MPtriethoxysilane) is not known to be used in sol-gel processing, and one is not a functional equivalent of the other. Instead, the chemistry of each of these mercapto silanes is substantially different, with 3-mercaptopopyl-tri-ethoxysilane decomposing to ethanol on contact with water or humidity.

SUMMARY OF THE INVENTION

Metal nano-clusters, such as silver, platinum, palladium, and gold nano-clusters, are synthesized on particles, which may be nano-sized or larger using a polyol process. For example, the metal nano-clusters are immobilized on MPTS-functionalized or 3-mercapto-tri-ethoxysilane-functionalized particles, such as silica or polystyrene, using a polyol such as ethylene glycol, diethylene glycol, trimethylene glycol, and isopropylene glycol. In one example, the process is a continuous process including the synthesis of the particles and formation of metal nano-clusters on the surface of the particles, without separating the particles from suspension, such as a one-pot, sol-gel-polyol process.

Field emission scanning electron microscopy (FE-SEM), UV-vis spectrophotometer and X-ray diffractometer (XRD) are used to characterize the composite particles. Process controls include the conditions for synthesizing particles with a functionalized surface, which allows control of the mean particle size and size distribution, and the conditions for synthesizing of metal nano-clusters on the surface of the particles. As will be seen in the examples, it is very difficult to control a one-pot, sol-gel-polyol process without control of all of the significant variables, including temperature, concentration of reactants, time for both the particle synthesis process and the process of metal ion reduction and nano-cluster synthesis. Additions must be made at the correct time and temperature to synthesize metal nano-clusters of a specific size and size distribution on non-agglomerated particles having functionalized surfaces.

The two processes of particle synthesis and metal nano-cluster deposition may be thought of as substantially separable and sequential in time, allowing any size and number density of particles and any size and number density of metal nano-clusters to be synthesized, as if conducted in independent processes. However, the sequence and timing of processing and the omission of any step of washing or separating out of the particles from the reactants that form them makes a continuous process both more difficult to successfully complete and much more economical in energy usage, time and processing costs, if successful. In one example, a product is produced that may be immediately mixed with a granulated polymer and extruded to form a master batch containing a concentrated, protective antimicrobial and antifungal silver nano-cluster—particle additive that is also non-leaching. The metal-particle complexes formed by this continuous process may be combined with a wide variety of polymers, rubbers, lipids, latex and co-polymers, such as polyethylene, polypropylene, nylon, vinyl, polyester, silicones, polyurethanes, acrylates, acrylic, celluloses, polysaccharides, latex. For example, the metal-particle complexes, still in a suspension and without separation or washing, may be added during processing or synthesis of such polymers, rubbers, lipids, latex and co-polymers or may be added later during an extrusion or die casting process by introducing the additive in a master batch.

By heating to an elevated temperature, volatile organic compounds may be driven off. Raising the temperature to 80° C. causes a color change, in one example, from a brown or dark yellowish color to a white or pale yellow color (depending on the size and size distribution of silver nano-clusters). A white or pale yellow additive may be used in colored paints and coatings without unduly influencing the final color of the paints or coatings.

By controlling processing temperature, time and the concentration, order of introduction and timing of introduction of additions, extremely small silver particle clusters in a narrow size range (or a narrow size distribution) and thickness may be immobilized on the surface of silica particles, which may also be very small and may be non-agglomerated. The nano-sized products are synthesized bottom-up and may be formed in situ. In one example, the silica particles, which may be nano-sized, are synthesized in a one-pot process, which includes the nucleation and growth of metal nano-clusters on the surface of the synthesized silica particles within the same batch process and a common vessel. This process reduces costs and prevents unwanted agglomeration, which occurs over time, while achieving structural improvements in the complexed silver-silica particles.

In one example, a one-pot polyol process for making particle complexes comprises synthesizing a plurality of particles in a sol-gel process to form a particle suspension, functionalizing the surface of the plurality of particles in the particle suspension, adding, without separating the plurality of particles from the particle suspension, a polyol to form a polyol suspension, mixing a source of metal ions into the polyol suspension, reducing the metal ions to form a metallic phase, and nucleating metal nano-clusters on the surface of the plurality of particles functionalized during the step of functionalizing, to form the particle complexes.

One advantage is the reduced number of steps for preparing a metal-particle complex having nano-sized crystalline clusters of metal bound to the surface of a particle. The entire particle complex may be nano-sized, or the metal clusters may be nano-sized and immobilized on silicon particles having a mean diameter greater than 100 nm. The reduction in cost compared to other known processes is very significant, making production of nano-sized composite particles for commercial purposes, such as inclusion in bulk polymers, agriculture, water treatment, antimicrobial paints and coatings, and others applications, cost effective. Yet another advantage is the improvement in metal cluster size and distribution on the surface of the silica particles, a reduction in particle agglomeration and stability of a particle complex suspension, which is improved under some processing conditions compared to separately synthesized silica particles that are introduced into a second batch process.

A one-pot process may be used to eliminate the necessity of separating and drying the base particles, which is an energy intensive process, and the need for pulverizing the particles to mitigate agglomeration during the separation process. Thus, a one-pot process may save energy compared to the process disclosed in Korean appl. no. 10-200400039256 as presented in the background. In addition, such a one-pot process may use less metal for the same effectiveness as the Oh Reference disclosed in the background, which produces metal colloids. An increased surface area per volume of metal added to a polyol process and decreased agglomeration of silver-silica particle complexes makes many heretofore impractical applications, such as adding silver-silica particle complexes to bulk materials, commercially practical.

In another example, a polyol process for making particle complexes may comprise synthesizing a plurality of particles in a sol-gel process to form a particle suspension, functionalizing the surface of the plurality of particles in the particle suspension with a mercapto-silane selected from the group of mercapto-silanes consisting of: a (3-mercaptopropyl) trimethoxysilane having the formula:

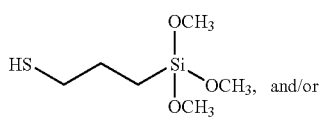

a (3-mercaptopropyl)triethoxysilane having the formula:

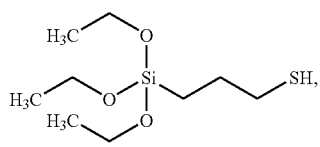

mixing the plurality of particles and a polyol to form a polyol suspension, adding poly(vinylpyrrolidone) to regulate the reduction and transfer of metal ions to metal nano-clusters and mixing until the poly(vinylpyrrolidone) is substantially dissolved, mixing a source of metal ions into the polyol suspension, reducing the metal ions to form a metallic phase, and nucleating metal nano-clusters on the surface of the particles functionalized during the step of functionalizing, while controlling the temperature, to grow the nucleated nanoclusters on the functionalized surface of the particles, to form the particle complexes.

One advantage is that the process for immobilizing metal nano-clusters on the surface of a particle may comprise a polyol process. Yet another advantage is that the polyol process may be controlled to provide an average metal nanocluster size of less than 10 nm, which increases catalytic activity of the nano-clusters of metal compared to larger sizes, without undue agglomeration of metal nano-clusters. Overcoming the severe, time-dependent agglomeration of metal colloids, which is especially pronounced for metal nanoparticles, is a major achievement that makes the suspensions stable or metastable at room temperature.

Yet another advantage is that a UV-vis spectrophotometer may be used to control the process by comparing measured spectra obtained from measurements during the process to a known, desired spectrum at a specific temperature and concentration of metal precursor.

Yet another advantage is that a non-leaching antimicrobial additive may be produced that comprises silver-silica particle complexes in a suspension mixed with a powdered polymer precursor or granulated polymer material that is formed by an extrusion process into a master batch additive. The silica particles may have functionalized groups immobilizing silver nano-clusters on the functionalized surface of the silica particles, such that the silver-silica particle complexes are stable in the suspension at room temperature, avoiding gelation of the suspension, prior to mixing with the polymer precursor or material. The powdered polymer precursor or granulated polymer material may be mixed with the suspension at a temperature of at least forty degrees centigrade, such that the silver-silica particle complexes are distributed throughout the precursor or material and water and volatile organic compounds are vented. Another advantage is that the process may be conducted at an elevated temperature of at least 80° C. to produce a substantially clear or white additive. Another advantage is that a master batch additive may have a mean concentration of silver, with substantially no ionic silver, in a range from fifty milligrams of silver per kilogram of master batch to one hundred fifty milligrams of silver per kilogram of master batch, for example. Thus, the master batch may be used to protect polymer articles from microbial and fungal growth on the surface or within pores, crevices and seams of the polymer article. Another advantage is that the polymer may be spun as a fiber or drawn as a sheet or film. Another advantage is that the polymer may be formed in a die injection molding process or an extrusion process.

A polymer container may comprise a polymer including silica-silver particle complexes, wherein the polymer is a polymer having a thickness and an oxygen permeability selected such that oxygen passes through the thickness of the polymer at a rate of at least 10,000 cubic centimeters of oxygen per meter squared per twenty-four hour period. One advantage is that the polymer container or film may prevent both aerobic and anaerobic bacterial growth on the container or film. Another advantage is that food within the container remains fresh longer. Yet another advantage is that the container is easier to clean and disinfect.

BRIEF DESCRIPTION OF THE FIGURES

The examples described and drawings rendered are illustrative and are not to be read as limiting the scope of the invention as it is defined by the appended claims.

DETAILED DESCRIPTION OF PREFERRED EMBODIMENTS OF THE INVENTION

The examples described and drawings rendered are illustrative and are not to be read as limiting the scope of the invention as it is defined by the appended claims.

Figure 15:
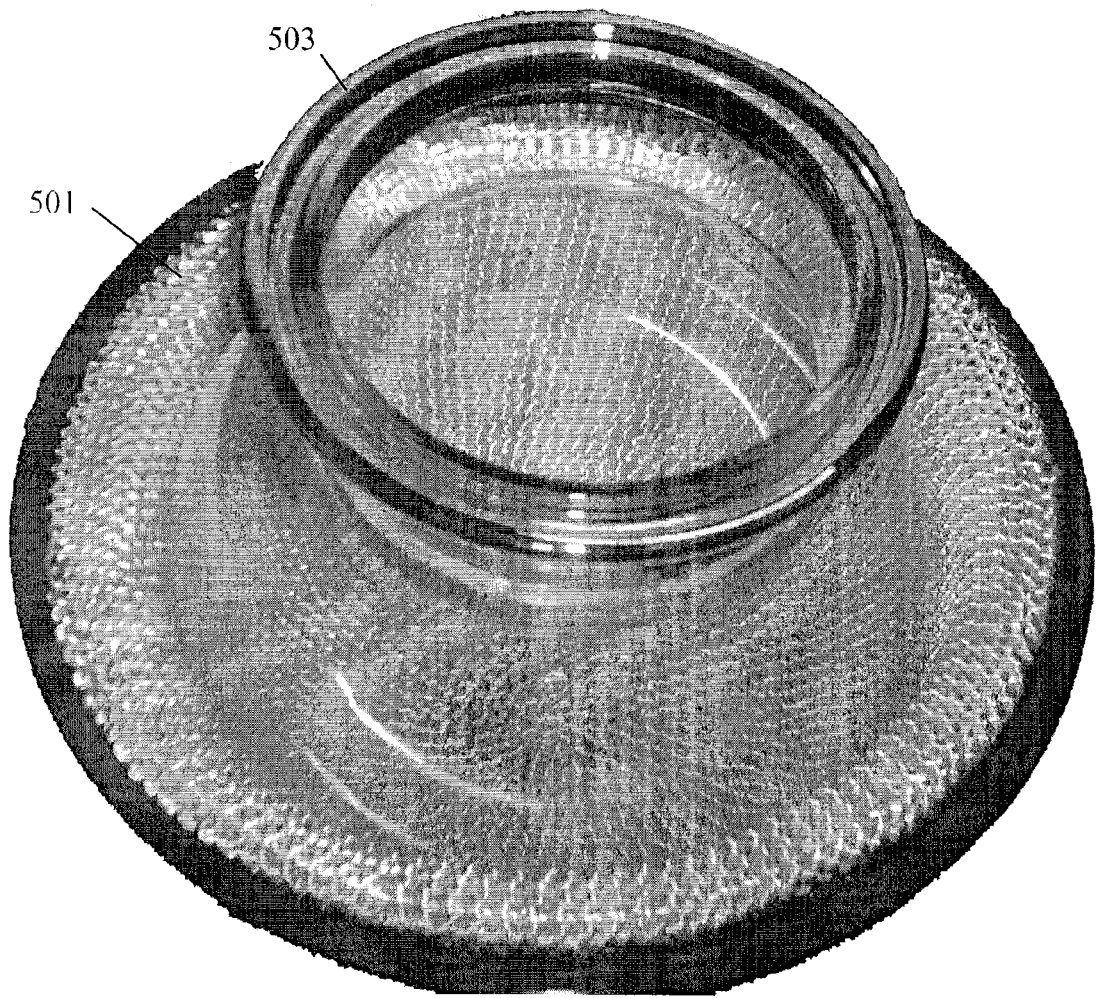
FIG. 15 illustrates a retort vessel 503 place in a hemispherical heater 501.
Figure 16:
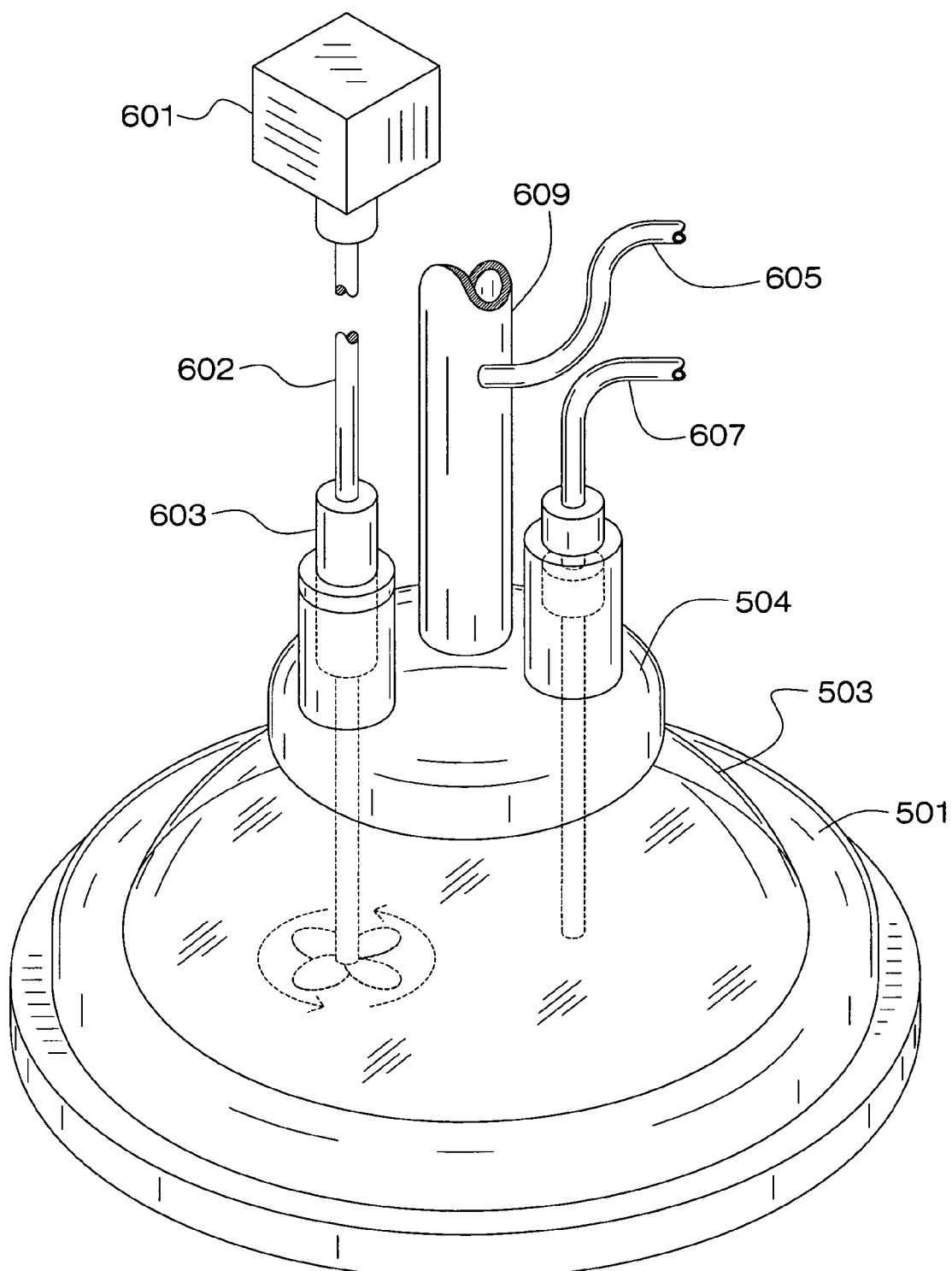
FIG. 16 illustrates the retort of FIG. 15 assembled for nucleation and growth of silver-silica particle complexes.

The equipment illustrated in FIGS. 15 and 16 show a hemispherical heater 501 heating a polyol suspension in a retort vessel 503. Signals of a temperature sensing device 607 may be monitored for purposes of process control for regulating the heating of the heater 501. The top 504 of the retort vessel closes and seals the retort. A long column 609 (partially shown) extends from the retort vessel and is cooled 605 by a cooling fluid, which condenses vapors from the retort vessel. An electric motor 601 rotates a shaft 602 connected to a pass-through sealed connector 603 to gently stir the polyol suspension in the retort vessel 503, the equipment keeping the temperature of the polyol suspension regulated and the polyol suspension mixed. A sampling port (not shown) may be included to take samples from the polyol suspension.

Tetraethyl orthosilicate (TEOS 98%, Aldrich), absolute ethanol (HPLC grade 99.9%, DUKSAN Pure Chemical Company, Korea) and ammonia solution ($NH_4OH$ 25%, Wako Pure Chemical Industries, Japan) may be used to synthesize silica particles. 3-mercapto-propyltrimethoxysilane (MPTMS), purchased from SIGMA, may be used to bind silica and silver particles, during the process. Silver nitrate ($AgNO_3$ 99.995%, Aldrich) may be used as a silver ion source; however, other sources of silver or other metals may be used as a source of metal ions. Platinum, gold, silver and other metal ions may be used to produce metal-silica particle complexes, which may include nanoparticles with nano-clusters of metal bound to the surface of a dielectric particle, such as polystyrene or silica. Ethylene glycol (Yakuri Pure Chemicals Company, Japan) and poly(vinylpyrrolidone) (PVP, K-15, Mw 10,000, Junsei Chemical Company, Japan) may be used to reduce silver ions in a polyol process. All materials are used as received. Water is deionized, such as by a Milli-Q Plus system (Millipore, France), having 18.2 MΩ electrical resistivity.

Spherically-shaped silica particles may be prepared by sol-gel process on the basis of Stöber method, such as described in W. Stöber, A. Fink and E. Bohn, *J. Colloid Interface Sci.* 26 (1968), p. 62. For a MPTS-functionalization of the surface of silica particles, a procedure similar to that described by Philipse and Vrij may be applied, such as disclosed in A. van Blaaderen and A. Vrij In: H. E. Bergna, Editor, *The Colloid Chemistry of Silica*, American Chemical Society, Washington, D.C. (1994), p. 83 (Chapter 4). While it is known to prepare spherically-shaped silica particles and to use the particles in later batch processes after separation of the particles, the development of a one-pot process for both preparation of the silica particles and further processing of the silica particles to form metal-silica particle complexes is not known. Examples of processing parameters capable of processing spherically-shaped silica particles in a one-pot process that achieves a unique metal cluster—silica particle complex microstructure are described in some specific examples of the process.

Figure 1:
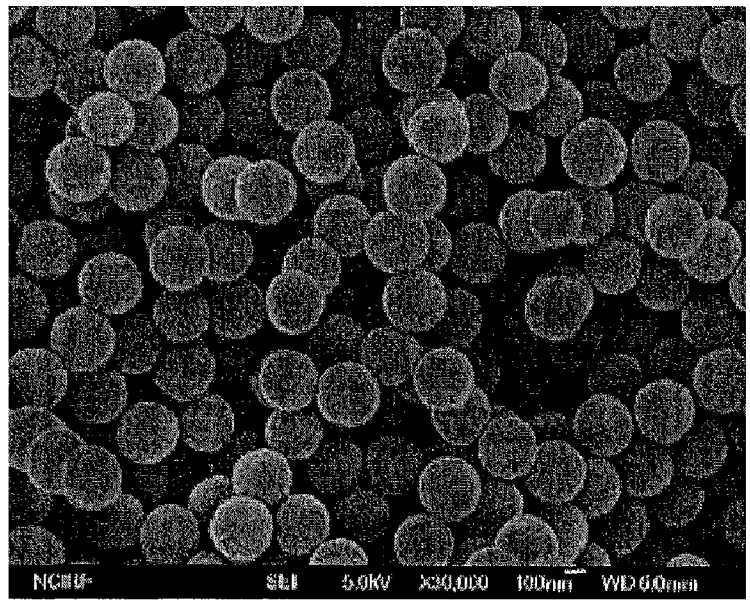
FIG. 1 shows an FE-SEM image of MPTMS-functionalized silica particles synthesized by a modified Stöber Method.

In one example, a mass of 10.6 grams of 25% ammonia solution is mixed with 125 grams of absolute ethanol while stirring moderately. After 20 minutes, a sol-gel reaction for the formation of silica particles may be initiated by adding 5 grams of the TEOS into the solution. After 1 hour, a mass of 1 gram of MPTMS is added into the solution. Moderate stirring for 6 hours creates silica particles functionalized with thiol groups, which may be separated from the solution by centrifuging at 3000 rpm for 30 minutes, for examination using electron microscopy, as shown in FIG. 1. Separated particles of silica may be washed with ethanol to remove un-reacted reagents. Then, the washed particles may be collected and dried at 40° C. for 1 day in an incubator. These particles may be stored until needed, if they are to be used in a multi-pot process or for characterization of the intermediate particle morphology.

In one example, without separating particles of silica from the solution, nano-clusters may be immobilized onto the surface of particles using a one-pot, polyol process. One example of a polyol includes use of an ethylene glycol. The silica particles, which may be nano-spherical particles may be functionalized with thiol groups dispersed in a polyol, such as an ethylene glycol. Sonication and agitation may be used to prevent agglomeration and to mix the polyol suspension. Then, PVP may be introduced into the mixture while stirring mildly to prevent undue distortion of polymer chains. The concentration of silica particles to PVP may be fixed at a ratio of 0.1 wt % silica particles to 4 wt % PVP, for example. After a period of time sufficient to completely mix and dissolve the PVP and ethylene glycol, such as a few hours to 1 day, an amount of silver precursor, such as $AgNO_3$, may be added to the solution, and the solution may be slowly stirred for 30 minutes in order to completely dissolve the $AgNO_3$. The solution is heated, such as in a reflux heater, for a desired temperature and time. Selection of the amount of $AgNO_3$, the temperature and time determines the size and thickness of the silver nano-clusters or layer of silver deposited onto the surface of the synthesized, thiol-modified silica particles.

Herein, the term one-pot is used throughout as a term of art. A one-pot process means a process that commences and completes within a common vessel. The common vessel may change from a smaller vessel to a larger vessel or otherwise, but it is the fact that substantially no intermediate processing is performed that makes the one-pot process a one-pot process. Changing from one vessel to another, without intermediate processing of the contents of the vessel is still a one-pot process. Substantially no intermediate processing means that the mixture from the first vessel is unchanged chemically, other than by chemical processing within a common vessel and by additions made to the mixture. Also, small amounts of the mixture may be removed from time to time for testing and quality control, and this is not considered substantial intermediate processing. Within the context of the examples, one example of substantial intermediate processing would be separating silica particles or thiolated silica particles from a solution, such as by centrifuging. A one-pot process does not include any step that substantially changes the mixture by separating out one component of the mixture for further processing in a separate batch process, but a one-pot process may include adding of ingredients or mixing of a first mixture into another mixture or ingredient, whether the mixture is transferred to a second vessel or otherwise. So long as the mixtures or ingredients are added to a common vessel, the process is a one-pot process, regardless of the number of transfers and the number of vessels used during the process.

For example, a one-pot process commences by synthesizing thiol-modified silica particles in a desired size range in a first vessel and then the entire ingredients of the first vessel, less a sample for testing, is transferred to a second vessel in which a polyol and $AgNO_3$ are added to commence the nucleation and growth of silver clusters on the surface of the silica particles. A surfactant, such as Tween 20 or the like, may be used to more effectively wet the particles, depending on the polyol selected. Preferably, no surfactant is necessary.

To investigate the formation and the morphological properties of silica-silver nanocomposite particles, field emission scanning electron microscopy (FE-SEM, JEOL JSM-6700F) was operated at acceleration, voltage of 5.0 kV. To obtain specimens for FE-SEM analysis, ethanol is added to silica-silver particles to form a suspension. Then, centrifugal force is applied at 3000 rpm for 20 minutes to separate out the particles. Separated particles were washed with ethanol two times. During the washing process, centrifugal force is applied at 3000 rpm for 20 min reducing the sedimentation time. Obtained particles were dried at 40° C. for 1 day in vacuum drying oven. Finally, platinum was sputtered for 3 minutes at 10 kV, depositing a very thin layer of platinum on the surface of the particles. The particles were then prepared for electron micrography.

UV-vis absorption spectra of the silica-silver particles may be used to characterize the particles prepared under a variety of processing conditions. A UV-vis spectrophotometer (Agilent 8435, Agilent Technologies) may be used, for example. Samples reported are diluted with ethylene glycol prior to measurement of the absorption spectrum at a volume ratio of 270 (ethylene glycol) to 30 (sample). Different ratios of dilution may be used, so long as the comparison between samples uses a consistent protocol for purposes of the comparison.

X-ray diffraction (XRD) is carried out using a Rigaku D/max-2500 X-ray diffractometer operating at 40 kV and 100 mA with the Cu K$\alpha$ radiation ($\lambda$=0.15418 nm) at a scanning rate of 2° min$^{-1}$ in 2$\theta$ ranging from 10° to 80°.

Spherically-shaped silica particles were prepared by sol-gel process on the basis of Stöber method, as previously described. It is believed that thiol groups are able to interact with silver ions by the cleavage of an S—H bond and the spontaneous formation of an S—Ag bond, such as suggested by Y. Cao, Y. S. Li, J. L. Tseng and D. M. Desiderio, *Apectrochim. Acta Part A* 57 (2001), p. 27, and P. N. Floriano, O. Schlieben, E. E. Doomes, I. Klein, J. Janssen, J. Hormes, E. D. Poliakoff and R. L. McCarley, *Chem. Phys. Lett.* 321 (2000), p. 175, for example for some metal-inorganic oxide bonds.

Other metal-metal oxide bonds may be facilitated using such thiol groups. Metals such as platinum, gold, palladium and others may be deposited on the surface of metal oxides and oxides using a thiol containing a sulfur atom. For example, as a result of unique behavior of thiol groups containing at least one sulfur atom, chemicals containing such thiol groups have been widely used as chemical protocols to make various metal-metal oxide composites as suggested in the following references: P. N. Floriano, O. Schlieben, E. E. Doomes, I. Klein, J. Janssen, J. Hormes, E. D. Poliakoff and R. L. McCarley, *Chem. Phys. Lett.* 321 (2000), p. 175; A. Dokoutchaev, J. T. James, S. C. Koene, S. Pathak, G. K. S. Prakash and M. E. Thompson, *Chem. Mater.* 11 (1999), p. 2389; J. H. Park, S. G. Oh and B. W. Jo, *Mater. Chem. Phys.* 87 (2004), p. 301; and J. H. Park, Y. G. Kim, C. Oh, S. I. Shin, Y. C. Kim, S. G. Oh and S. H. Kong, Mater. Res. Bull. 40 (2005), p. 271. However, none of the references are capable of making the metal cluster-silica particle complexes in a one-pot process having microstructures of the examples observed using electron microscopy or having stability against gelation at or substantially above room temperature.

In one example of a process to prepare silica-silver nanocluster particles, thiol groups are introduced by graft reactions between surface silanol groups of synthesized silica particles and MPTMS. An FE-SEM photograph of silica particles functionalized with thiol groups is shown in FIG. 1, for example. In this figure, mono-dispersed silica particles with a spherical shape and an average particle size of about 320 nanometers (nm) in diameter are observed. Using the synthesis process described, other diameters may be selected based on the synthesis reaction time, concentration of silica precursor and temperature. In one example, silica particles with thiol groups are produced having an average diameter in a range from 20 to 40 nanometers.

Figures 2A, 2B:
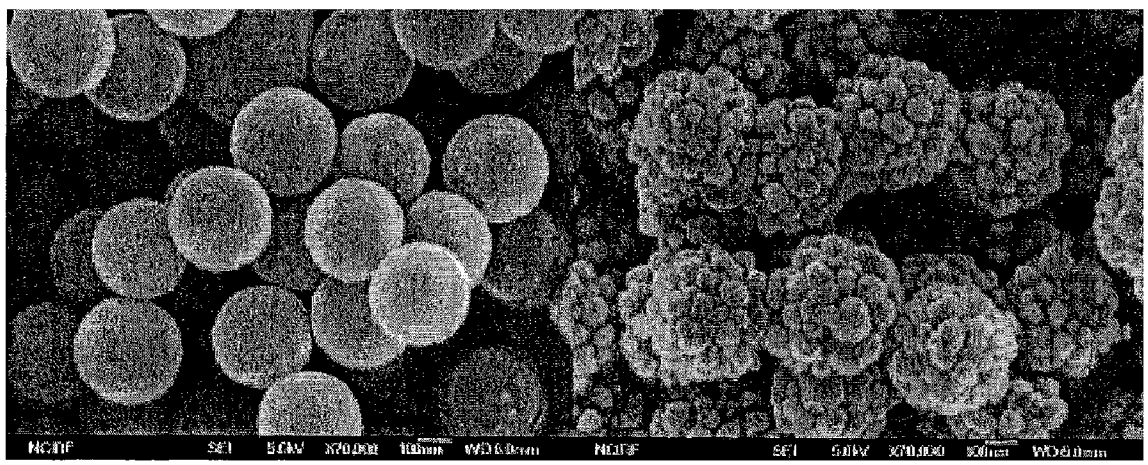
FIGS. 2A and 2B compare FE-SEM images of an example of a silica-silver composite particles prepared using a polyol process at 120° C. for 4 hours with silver concentration of 1000 ppm (FIG. 2A) in the absence of PVP and (FIG. 2B) in the presence of PVP.

A polyol process is used to form and immobilize silver nanoparticles onto silica surfaces functionalized with thiol groups, such as in a one-pot process. In this process, it is believed, without being limiting, that PVP acts not only as a nucleation-promoting agent for silver ions but also as a stabilizer for silver nano-clusters during the polyol process. The resulting microstructure is shown in FIG. 2A, without PVP, and FIG. 2B, with PVP (all other processing variables held constant). Heating ethylene glycol solution containing 1000 ppm silver ions and silica particles functionalized with thiol groups with a reflux at 120° C. for 4 hours in the absence of PVP forms only a few particles immobilized onto the silica particle surface, as shown in FIG. 2A. However, when the same reaction conditions proceeded in the presence of PVP, silver nanoparticles were successfully formed and immobilized onto the surface of silica particles as shown in FIG. 2B.

Figure 3:
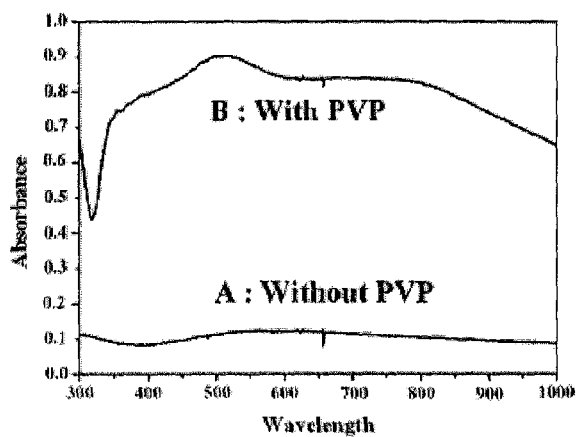
FIG. 3 compares a UV-vis absorption spectra of the silica-silver composite particles prepared by polyol process at 120° C. for 4 hours with silver concentration of 1000 ppm (A) in the absence of PVP and (B) in the presence of PVP.

Results of UV-vis absorption spectra are shown in FIG. 3, and clearly show a significant difference attributable to the formation of the silver nano-clusters on the surface of the functionalized surface of the silica particles. The absorption spectra show a substantial difference between the process (A) without PVP and (B) with PVP. Curve A shows very weak absorption intensity, whereas curve B shows a broad absorption band about 520 nm, red-shifted compared to the general absorbance band of silver nano-particles observed at about 400 nm. Generally, absorption and scattering of light by a particle is known to depend on the particle's chemical composition, size, shape, surrounding dielectric medium and coupling of the colloids and adsorbed solutes, as described in A.

Slistan-Grijalva, R. Herrera-Urbina, J. F. Rivas-Silva, M. Ávalos-Borja, F. F. Castillón-Barraza and A. Posada-Amarillas, *Physica E* 27 (2005), p. 104, for example.

Especially, in the case of composite particles consisting of dielectric core and a metal layer, when the thickness or coverage of a metal layer is increased, the plasmon peak broadens, red-shifts, and depresses the scattering peak greatly. Mie's scattering theory may be able to explain this effect, as disclosed in G. Mie, *Ann. Phys.* 25 (1908), p. 377; and D. S. Wang, M. Kerker and H. Chew, *Appl. Opt.* 19 (1980), p. 2135. The red-shift and broadening of the plasmon peak is useful to identify and control the process of metal nucleation and cluster growth on the functionalized surface of the dielectric particles, such as silica. For example, the red-shift and broadening of the Plasmon peak may be used during a one-pot process to control the time-temperature-concentration sensitive nucleation and growth of silver clusters on thiol functionalized silica particles. The test is simple to perform and rapid, which allows for its use during the synthesis process. A profile of the plasmon peak may be compared to a desired structure of the silver nano-clusters on a particle. In one simple use, a process is continued until the measured profile matches a desired profile. Then, the process is stopped. For example, the process may continue until the peak maximum of a measured profile is at least the same as the peak maximum of a target profile, a width at half maximum of the peak is the same or greater or lessor than a target profile, or both thereof. Failure to achieve process control specifications within a certain time period, such as 24 hours, may be used to identify irregularities requiring further characterization or rejection of a batch. The measured profiles correlate well to observed FE-SEM images. As a result of measurements conducted over time and many batches, the measurements confirm that PVP successfully promotes stable formation of silver nano-clusters on functionalized silica particle surfaces.

Varying reaction temperature and time has an effect on morphology of the silver-silica composite particle. In theory it should be possible to separate the stages of nucleation and growth of metal clusters on the surface of a substrate particle, such as suggested by N. Toshima (first ed.), Ed.: T. Sugimoto, *Fine Particles: Synthesis, Characterization, and Mechanisms of Growth* vol. 92, Marcel Dekker Inc., New York (2000), p. 461 (Chapter 9.2). There may be an additional advantage of separating the process of nucleation from the growth process during the preparation of composite particles consisting of a dielectric core and a metallic shell, because the formation of large aggregates or particles is reduced compared to other processes, as disclosed in M. Schierhorn and L. M. Liz-Marzán, *Nano Lett.* 2 (2002) (1), p. 13.

Figures 4A, 4B:
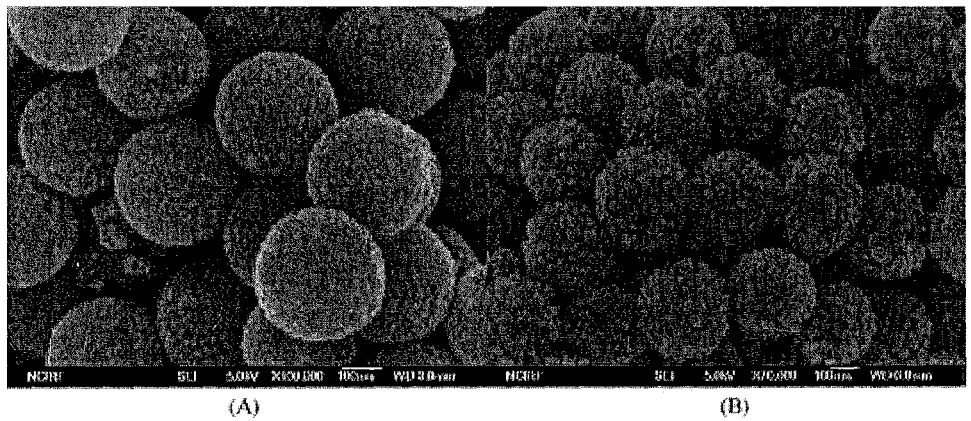
FIGS. 4A and 4B compare FE-SEM images of the silica-silver composite particles prepared by polyol process with silver concentration of 1000 ppm for (FIG. 4A) at 25° C. for 12 hours and (FIG. 4B) after additional growth for 7 hours with increasing reaction temperature.

To immobilize silver nano-clusters with small size and narrow size distribution onto the surface of silica particles, a reaction may be conducted at a comparatively low temperature and for a relatively long time, which is counter-intuitive. For example, an ethylene glycol solution containing silica particles, $AgNO_3$, and PVP is maintained at 25° C. for 12 hours using mild stirring. FIGS. 4A and 4B compare FE-SEM image of the resulting composite particles in FIG. 4A with composite particles in FIG. 4B, which continues the reaction in FIG. 4A while increasing the processing temperature. FIG. 4A shows images of a large number of silver nano-clusters having a small size and being immobilized on the surface of the silica particles, suggesting good nucleation and relatively slow growth (and low degree of ripening—a time dependent coarsening where large particles grow at the expense of smaller particles driven by surface energy reduction). Subsequently, the reaction temperature was increased up to 120° C. in stages as follows: (i) temperature was increased to 40° C. and maintained for 4 hours, (ii) increase to 60° C. for one hour, 90° C. for one hour, and 120° C. for 1 hour, while the reaction continued. FIG. 4(B) shows the resulting FE-SEM image. The size of silver particles is homogeneously increased while maintaining a comparatively narrow size distribution.

Figure 5:
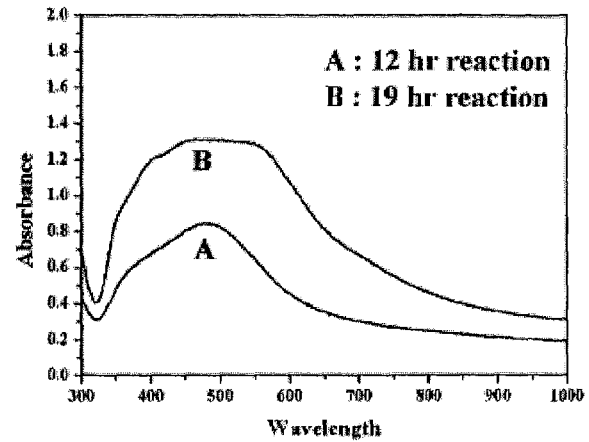
FIG. 5 displays a graph of the UV-vis absorption spectra of silica-silver composite particles prepared by polyol process with silver concentration of 1000 ppm; at (A) 25° C. for 12 hours and (B) after additional growth for 7 hours with a staged ramping of the reaction temperature.

UV-vis absorption spectra of the silica-silver composite particles of (A) FIG. 4A and (B) FIG. 4B are shown in FIG. 5. In the first curve A, a broad absorption peak appears about 490 nm, which confirms that very small silver nano-clusters are immobilized onto the silica surface. After additional growth of silver particles, a much more distinct peak is shown in the second curve B indicating an increase in size of the silver nano-clusters. Moreover, it is thought that the thickness of silver layer increases with growth at the higher temperature. This result correlates well with observations of the FE-SEM images. By separating a first nucleation phase, in which a large number of nano-clusters are formed, and a growth phase, in which the nucleated nano-clusters grow in size, a multitude of nanoclusters may be formed. The nanoclusters may have a relatively narrow size distribution. In one example, silica particles have mean hydraulic diameters in a range from 10-100 nanometers, more preferably 30-40 nanometers. The silica particles may have a comparatively narrow size distribution, such as a standard deviation of 20 nanometers at one standard deviation of the mean. The mean size of silver (or other metal) nano-clusters is more difficult to determine and must be calculated from observations, such as by observations of X-ray diffraction, for example. A qualitative or quantitative distribution of the mean size may be compared by comparing UV-vis data.

The two steps of nucleation and growth are completed in a one-pot, polyol process. The slower and more easily controlled reaction rate of the polyol reduction method provides a surprising and unexpected control of the metal nano-cluster size and the silica particle size. For example, nano-clusters may have 5-9 atoms in isolated clusters of metal atoms on a functionalized surface of a particle, such as a silica particle or a polystyrene particle. Known chemical reduction methods, using a reducing agent such as hydrazine or sodium borohydride, fail to control the size and distribution effectively. Thus, a polyol process according to examples of the present invention is a substantial improvement over any previous method for producing particles of silica with metal deposits on the surface.

Figures 6A, 6B:
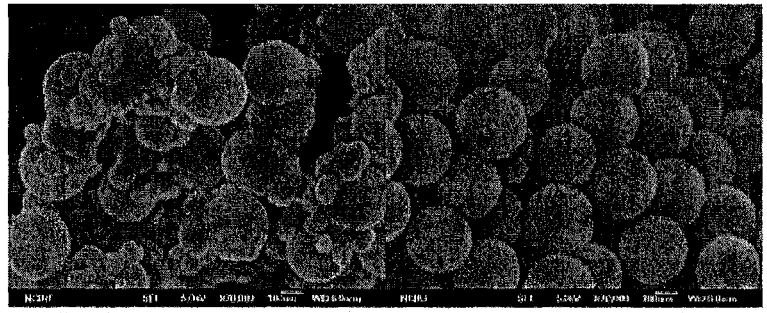
FIGS. 6A-6C compares FE-SEM images of silica-silver composite particles prepared using a one-pot, polyol process and a silver concentration of 10,000 ppm at (FIG. 6A) 120° C. for 4 hours, (FIG. 6B) 25° C. for 12 hours and (FIG. 6C) after additional growth for 7 hours with increasing reaction temperature.
Figure 6C:
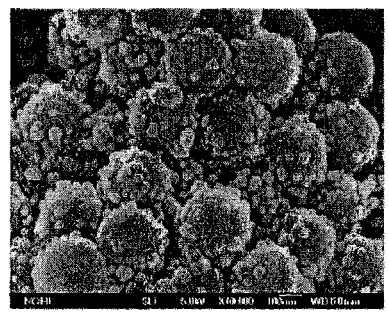

In one example, a higher concentration of $AgNO_3$ (e.g. 10,000 ppm) is used. In this example, a two-stage nucleation and growth process is used to control both size and distribution of sizes of the silver nano-clusters on the surface of functionalized silica particles, with a resulting micrograph shown in FIG. 6B. In another example, a reaction was conducted at 120° C. for 4 hours, which produced few silver particles with extremely large size, as shown in the images of FIG. 6A. In comparison, a process including a controlled nucleation phase at 25° C. for 12 hours gave sufficient time for nucleation of more silver nano-clusters, as shown in FIG. 6B. Due to the comparatively high concentration of silver precursor (e.g. 10,000 ppm), the size of the nano-clusters of silver is substantially greater than the size of the nano-clusters grown at a concentration of 1000 ppm and the same temperature, as shown in FIG. 4A. The higher concentration makes it easier to nucleate and grow small silver clusters with a narrow size distribution at a low reaction temperature. The image in FIG. 6C shows an image after additional growth steps proceeding at staged, increasing reaction temperatures up to 120° C., using the same protocol as the reaction in FIG. 4B. The image in FIG. 6C shows that conditions suitable for growth at a lower concentration are not suitable for growth at a much higher concentration. Instead, the microstructure in FIG. 6B represents a nearly fully developed silver-cluster structure during the nucleation phase at the higher concentration of silver. In this example, it is believed that such high concentrations of silver require lower reaction temperatures and/or times for the growth phase. The resulting silver-silica particles are strikingly different than the images of FIG. 4B. After the staged ramping protocol for the temperature, the size of individual silver clusters immobilized onto the surface of silica particles is observed to increase irregularly and in reduced numbers of particle clusters. It is thought, without being limiting, that the slow reaction rate of the polyol process at low concentrations of silver precursor is accelerated at higher concentrations of silver precursor. Also, large clusters may be detached from silver particles, either mechanically or under solutal-thermal surface tension forces or both. Finally, rapid ripening may lead to growth of comparatively large silver clusters at the expense of smaller silver clusters, such as observed in Ostwald Ripening.

During the staged ramping of temperature with 10,000 ppm of silver precursor, a yellow substance is deposited on the reactor vessels walls. It is thought that the higher temperatures and comparatively high concentration of silver precursor cause very large silver clusters to form into silver particles that eventually detach from the silica particles. It is thought that large silver clusters become too large to be immobilized onto the surface of the silica particles by the thiol groups. Large particles of silver, about 50 nm in diameter or greater, are more easily dislodged from particles and plated onto the inside surface of the glass reactor vessel. Thus, evidence of deposits on vessel walls is an indicator of excessive silver concentration at a temperature greater than the desired nucleation and growth temperature.

Figure 7:
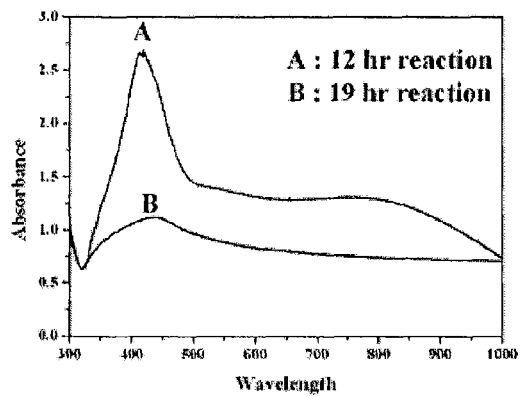
FIG. 7 displays graphically UV-vis absorption spectra for the silica-silver composite particles prepared by polyol process with the silver concentration of 10,000 ppm; at 25° C. for (A) 12 hour reaction, such as described for the reaction resulting in the image of FIG. 6B, and (B) after additional growth for 7 hours with increasing reaction temperature, such as described for the reaction resulting in the image of FIG. 6C.

In FIG. 7, the loss of mass from the surface of the silica particles during subsequent staged, ramping of the temperature is confirmed using the measured UV-vis absorption spectra of the samples shown in FIGS. 6B and 6C. In FIG. 7, a distinct, maximum peak intensity is shown in the curve labeled A, which corresponds to the image shown in FIG. 6B. The peak is less distinct in the curve labeled B, which shows the UV-vis absorption spectra after additional growth using a staged, ramped temperature to 120° C., as shown in FIG. 6C. The UV-vis absorption spectrum in the curve labeled A is preferred to the one labeled B, because the curve labeled A indicates that the thickness of silver nano-clusters is greater and the size distribution is more uniform (width of the peak). Now, comparing FIGS. 7 and 5, the higher concentration of silver nucleated and grown during the nucleation phase A of FIG. 7 provides a more uniform size distribution of silver clusters than either of the profiles shown in FIG. 5. Thus, it is believed that higher concentrations of silver and lower temperatures are preferred for nucleation and growth of silver clusters having uniform size distributions. A different staged, ramped temperature profile, such as having a lower maximum temperature or shorter stage time may be used to achieve better results with less plating out of silver, even at 10,000 ppm of silver precursor, for example, if a lower growth temperature is selected. Preferably, a balance is achieved between the concentration of silver in the polyol solution and the temperature-time profile used to nucleate and grow silver clusters, such that silver clusters are nucleated and grown having suitable uniformity for an application without wasting silver.

If metal clusters having small, uniform size distributions are desired, then it is believed that this may be achieved by controlling the concentration of metal ions, the temperature of nucleation and growth, and the time allotted for nucleation and growth. Higher concentrations with lower temperatures are thought to produce narrower cluster size distributions than comparably lower concentrations with higher temperatures for growth. Higher metal concentrations increase costs, however. As a result, there may be an optimal range for any desired application, depending on the metal cluster size distribution desired for a particular application. Specifications for very narrow cluster size distributions may increase the cost of production compared to specifications more tolerant of wider cluster size distributions. For example, it may be desired to have gold atom clusters of 5-9 atoms formed on a functionalized surface of a particle; therefore, a higher concentration of gold may be used during nucleation and growth, with nucleation and growth both occurring at comparatively low temperatures, such as in a range from 25 degrees centigrade to 40 degrees centigrade, more preferably keeping both at 25 degrees centigrade in one example. Based on cost considerations, a lower concentration of metal ions capable of producing a desired range of cluster sizes, by having a period of nucleation followed by a period of growth, is preferably to a higher concentration that yields a smaller percentage of metal in metal clusters compared to the amount of metal added to solution. To minimize costs of materials, it is preferable to use a protocol capable of depositing all or substantially all of the silver in solution on the surface of dielectric particles. Practical considerations may balance cost of materials with costs of processing, however. Cluster size distribution requirements may demand a higher cost of materials to achieve a desired cluster size distribution or a particular UV-vis absorption spectra. In each application, a desired uniformity and dispersion of particle size and metal nano-cluster size shall dictate the specific processing conditions.

X-ray Diffraction (XRD) Measurement of the Composite Particles

Figure 8A:
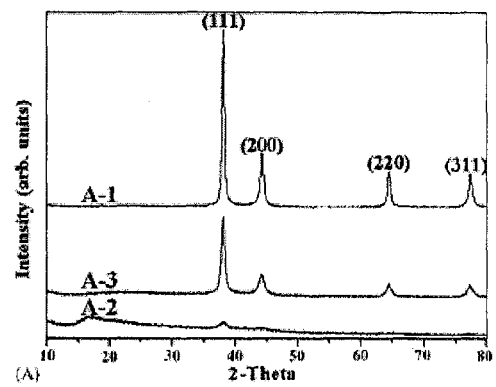
FIG. 8 compares XRD patterns of silica-silver composite particles prepared using a polyol process with silver concentration of (FIG. 8A) 1000 ppm and (FIG. 8B) 10,000 ppm; and (A-1, B-1) at 120° C. for 4 hours, (A-2, B-2) at 25° C. for 12 hours, (A-3, B-3) at 25° C. for 12 hours and additional growth for 7 hours with staged ramping of reaction temperature to 120° C.

XRD patterns of samples prepared at silver concentration of 1000 ppm are shown in FIG. 8A. In this figure, the crystalline nature of silver nanoclusters prepared at 120° C. for 4 hours A-1 will be well demonstrated by the diffraction peaks that match a face-centered cubic (fcc) phase of silver metal. The peaks at 2θ=38.11, 44.35, 64.45 and 77.41° are assigned as the (1 1 1), (2 0 0), (2 2 0) and (3 1 1) reflection lines, respectively, corresponding to the fcc crystal structure of silver metal. The average crystallite size of silver nanoparticles was also determined from the width of the reflection according to the Scherrer formula $D=0.9\lambda/(\beta \cos \theta)$, where $\beta$ is the full width at half-maximum (FWHM) of the peak, $\theta$ the angle of diffraction and $\lambda$ is the wavelength of the X-ray radiation (0.15418 nm), as disclosed in C. Suryanarayana and M. Grant Norton, X-Ray Diffraction: A Practical Approach, Plenum Press, New York (1998) p. 207. The crystallite size (value of D) calculated from the (1 1 1) reflection of the cubic phase of silver was 8 nm. However, this estimate of average size does little to determine the dispersion of sizes.

For the sample prepared at 25° C. for 12 hours, FWHMs of all peaks A-2 were broadened and peak intensities were low, which suggests an extremely small crystallite size, which is considered too small to calculate using the data obtained. After additional growth for 7 hours using the staged ramping of temperature to 120° C., the diffraction peaks A-3 clearly appeared and intensities were increased. This result indicates nucleation of very many silver nano-clusters and growth of the nano-clusters during staged ramping of temperature. Nevertheless, the mean crystallite size of the silver nano-clusters using staged ramping of temperature was about 8 nm, which is similar to the mean crystallite size calculated for silver clusters nucleated and grown using a temperature of 120° C. for 4 hours. Again, average crystallite size does not indicate anything about crystallite size distributions.

Figure 8B:
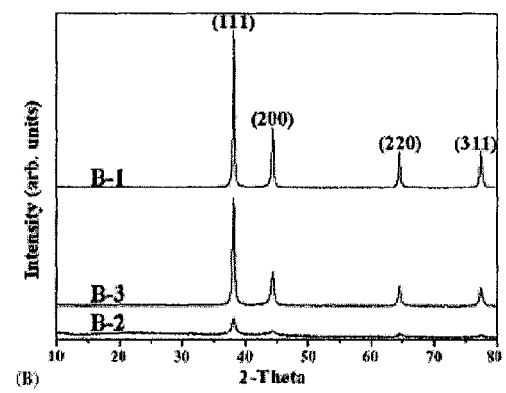
Figure 10:
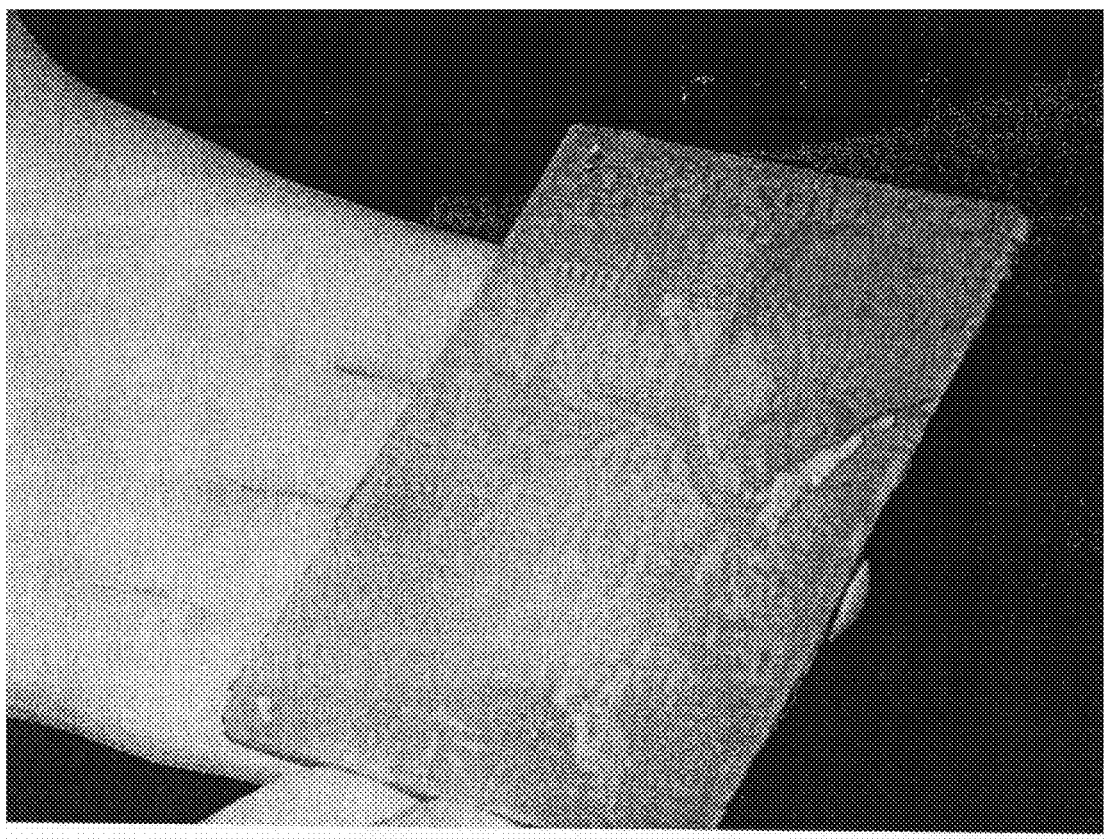
FIG. 10 illustrates a sample of a polymer including silver-silica particles having nano-clusters of silver within the polyethylene matrix, prepared for laboratory testing of antimicrobial properties using an agar coating and a seal used in e-coli testing protocol.

The XRD patterns of samples prepared at a silver precursor concentration of 10,000 ppm are shown in FIG. 8B. The crystallite nature of silver nanoparticles prepared at silver concentration of 10,000 ppm showed very similar trend to those of samples prepared at silver concentration of 1000 ppm. The crystallite size of all samples, determined by Scherrer equation using FWHMs, was calculated to be about 8 nm. The images shown in FIGS. 6A-C and UV spectra analysis suggest that the standard deviation is much less for a sample prepared at a comparatively high concentration and at 25° C. for 12 hours B-2, but the mean crystallite size is about the same as using a lower concentration of silver, provided that adequate time is provided at a growth temperature higher than 25 degrees centigrade.

In one example, a one-pot process is used to both synthesize silica particles and to bind nano-sized clusters on the surface of the synthetic silica particles using a common vessel. Nanoparticles of silica are formed and clusters of metal are synthesized on the functionalized surface of the silica particles. Poly(vinylpyrrolidone) is added to control the nucleation and growth of the metal clusters on the surface of the silica particles. A silver nitrate is used as a source of silver metal ions, which are reduced by the polyol. The reduced ions of silver are bound to the functionalized surface of the synthesized silica particles. Thiol groups provide a sulfur bond to bind the silver to the surfaces of the synthesized silica particles. In this example, the silica nanoparticles are nucleated and grown to about 30-40 nanometers, and 1,000 ppm of $AgNO_3$ precursor is added. A two-step temperature profile nucleated and grew silver clusters bound to the surface of the silica particles, as previously disclosed.

In yet another example, platinum ions are reduced from hexachloroplatinate (IV) hydrate (e.g. $H_2PtCl_6.xH_2O$, x=5.6, such as from Kojima Chemicals) using ethylene glycol and ethanol. Poly(vinylpyrrolidone) (e.g. PVP, K-15, MW 10,000 from Junsei Chemical Co.) may be used to nucleate and control the growth of platinum nano-clusters. In one alternative example, the platinum ions were bound not to silica nano-particles but to spherically-shaped polystyrene particles synthesized from a styrene monomer and a 4-styrene sulfonate sodium salt, as a co-monomer, and a sodium hydrogen carbonate, which was used as a buffer. The co-monomer provided sulfonate groups for binding with metal ions, such as the platinum ions of the example.

For example, a flask is charged with 30 grams of styrene monomer, 0.18 grams of 4-styrene sulfonate sodium salt, 0.15 grams sodium hydrogen carbonate, 0.15 grams of KPS and 270 grams of deionized water, which is stirred for 1 hour at room temperature. The mixture is heated in a thermostatic bath maintained at 80 degrees C. Polymerization proceeds for 24 hours under a nitrogen atmosphere, at a stirring rate of 350±1 rpm throughout the reaction period.

Then, a ratio of 0.1 gram of polystyrene aqueous colloid suspension (e.g. 10 wt %) and 2 grams of PVP are dissolved in 97.8473 grams of ethylene glycol or ethanol/water in a 1:1 ratio by weight. The hexachloroplatinate (IV) hydrate is added to the solution at a mass of 0.0527 grams and dissolved after 15 minutes of stirring, prior to heating the solution. A range of temperature from about 75 degrees C. to about 95 degrees C. achieved satisfactory results. A time for synthesizing the nano-clusters may be selected between about 1.5 hours to 8 hours, or longer. The satisfactory range of temperatures and times may increase or decrease based on changes in the ratio of polystyrene aqueous colloid suspension to hexachloroplatinate (IV) hydrate. It is expected that a higher ratio of polystyrene aqueous colloid suspension to hexachloroplatinate (IV) hydrate may prefer a higher temperature and/or longer time for nucleation and growth of platinum nano-clusters bound to the spheroidal polystyrene particles by sulfonate groups on the functionalized surface.

In still another example, a silver nitrate is used to bind silver nitrate nano-clusters on the surface of polystyrene spheres prepared as previously presented in the example for platinum, for example. This process may use the same process parameters as in the previous example for platinum catalyst nano-clusters, except that the ratio of silver nitrate to polystyrene aqueous colloid may be increased substantially. For example, 10 ml of the polystyrene aqueous colloid suspension (1000 ppm) and 2 wt % of PVP were completely dissolved in 88 grams of ethylene glycol. Then, 0.1575 grams of silver nitrate was added and stirred for 15 minutes. The temperature of the solution was increased to 90 degrees C. with reflux In yet another example, a silica sol is synthesized in a one-pot process as previously presented. A 3-mercapto-propyl-methoxysilane is used as before, together with a silver nitrate, ethylene glycol and water. The amounts used are 2.035 kg of silica sol, 54 grams of MPTMS, 102 grams of silver nitrate, 475 grams of ethylene glycol and 2.762 kg of water. Otherwise, the temperatures and reactions times may be selected and monitored as previously discussed, for example. In another example, 1.92 kg of silica sol, 51 grams of MPTMS, 51 grams of silver nitrate, 2.605 kg of water and 448 grams of ethylene glycol are used.

In yet another example, a 3-mercaptopropyl-ethoxysilane (MPtriethoxysilane) is used with a silver nitrate, ethylene glycol and water. Otherwise, the temperatures and reaction times remain within the same operative ranges. As a result, high temperature stability of the silver nano-cluster silica nanoparticle composite suspension is greatly improved compared to the use of 3-mercaptopropyl-trimethoxysilane (MPTS), which caused an unstable formation of a gel over time at room temperature. Providing for room temperature storage and shipping is a substantial improvement that was not expected by changing to MPtriethoxysilane. The increase in stability is a surprising and unexpected result, which was only identified after years of efforts to discover a process that could produce a suspension that remained stable at room temperature for extended periods, without gelation. Previously, suspensions were stored in refrigeration. Substitution of an ethoxy silane for the methoxy silane of Example 5 substantially improved stability at room temperature of the suspension.

In one example, a platinum colloid suspension is added to a suspension of silver nano-clusters bound to the surface of silica nanoparticles. Alternatively, platinum nano-crystals may be added, either on separate particles or on the same particles as the silver nano-clusters. It is thought that the platinum improves the stability of the silver nano-cluster silica particles, perhaps preventing fouling of the silver over time such as when used as an additive in a polymer article, for example. The platinum colloid may be prepared by mixing hexachloroplatinic (IV) acid hydrate (e.g. 0.764 grams), poly (vinylpyrrolidone) (PVP) (e.g. 37 grams) and diethylene glycol (726.236 grams). The diethylene glycol reduces the platinum ions to platinum and the PVP helps control the nucleation and growth of a platinum colloid suspension. Temperatures and times for processing the colloids depend on the mean diameter and standard deviation desired. A temperature of at least 90 degrees C. may be used, for example. In one example, platinum nanocrystals are first nucleated on the functionalized surface of silica particles and then silver nanocrystals are added by introducing silver nitrate in a common vessel.

In another example, white silver-silica particles are prepared having antibacterial and antifungal properties. A silica colloid suspension is prepared, such as one of colloid particles of 30-40 nm in diameter, as previously described, which may be prepared in a one-pot process. A white color has not been previously attainable for silver colloids. A white color is preferred for additives such as polymers, paints, coatings and sealants. Silver nano-clusters are bound to the surface of silica nanoparticles. Preferably, the silica nanoparticles comprise silica nanoparticles of 30-40 nm. The phase of nucleation and growth of metal clusters includes the use of a 3-mercaptopropyl tri-methoxysilane or -ethoxysilane, $NaBH_4$, and/or ascorbic acid functionalization of the silica surface and reduction process. A liquid phase synthesis allows low temperatures less than 30 to 40 degrees C. for synthesis of silica particles compared to the high temperatures of any gas phase synthesis. Thus, the silica colloid may undergo synthesis under stable conditions. A pH of greater than 8 and less than 12 is maintained. In one example, a pH of 10-11 is established for bonding of the silica colloid to silver nano-clusters. For example, 3-mercapto-propyl-trimethoxysilane becomes hydrated and binds onto the surface of the silica particles and the silver nano-clusters bind to the sulfur groups on the functionalized silica surface. the suspension is centrifuged or otherwise separated and particles are dried. During the drying process, the temperature of the silver-silica nano-particles is raised to 80 degrees C., and the color of the nanoparticles changes to white. In one example, the amount of silver to silica is 1.55 wt % of silver to silica and the amount of sulfur to silica is 0.1% of sulfur to silica. In another example, either $NaBH_4$ and/or ascorbic acid is used as a reducing agent, and the mass of silver to sulfur is in a range from 1.08 wt % to 0.55 wt %, and the mass of sulfur to silica is in a range from 0.05% to 0.25%. The heating of the resulting nanoparticles of this example to 80 degrees C. produces a white or only slightly yellow powder or liquid suspension. Without heating to 80 degrees centigrade, the nanoparticle suspension may appear gray, brown or dark yellow. In one example, the heating to 80 degrees centigrade occurs during processing when mixed with polymer resin, a co-polymer or in a master batch process.

Figure 9:
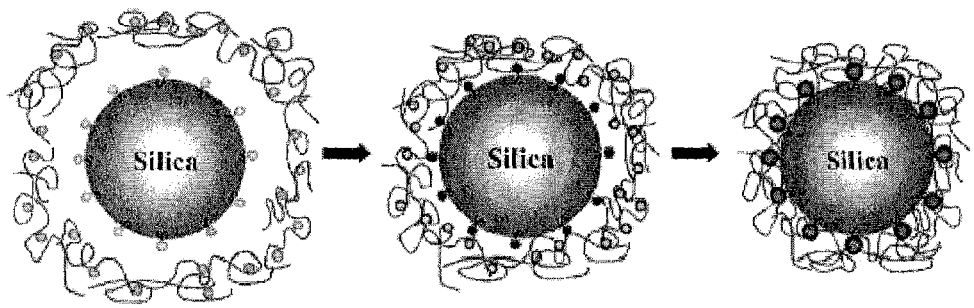
FIG. 9 illustrates a schematic representation of a mechanism for the immobilization of the silver nanoparticles onto a silica surface using a polyol process.

FIG. 9 illustrates, schematically and theoretically, a process of PVP-controlled nano-clustering of silver on a sulfur-group functionalized silica particle surface. In step one, PVP and silver ions are introduced into a vessel having thiol functionalized silica particles or nanoparticles. In step two, ions of silver migrate to the surface of the silica and are immobilized by the sulfur functional groups. In step 3, nano-clusters of silver are nucleated at sulfur bonding sites. This polyol process of controlling the rate of nucleation and growth makes repeatable and stable processing of metal nano-clusters possible on dielectric particles with a functionalized surface by controlling the concentration of metal ions, the temperature and the time for nucleation and growth. At an initial stage of the reaction, MPTMS-functionalized silica particles are synthesized, in one example, within ethylene glycol. Then PVP is dissolved into the ethylene glycol in a common reaction vessel. After substantially complete dissolution of PVP, $AgNO_3$ is added into the one-pot system. In this stage, silver ions are bonded with thiol groups of the silica surface by the cleavage of an S—H bond and the spontaneous formation of an S—Ag bond. Excess silver ions form complexes with PVP molecules by interaction between the hydrophilic pendant rings of PVP and the silver ions. In the second stage, $Ag^+$ ions are reduced to $Ag^0$ metal state in the ethylene glycol and PVP, in a polyol process. Silver nuclei form on the surface of the MPTMS-functionalized silica particles; nuclei are created at the silver ions, which act as seeds and are bound to the thiol groups on the surface of silica particles. Then, silver nano-clusters grow on the silica surface. Reduced silver species such as silver atoms or clusters in the solution are deposited on the nuclei immobilized on the silica surface. In one example, the slow reduction rate of the polyol process is preferred compared to the difficulty of controlling a general chemical reduction method using a reducing agent such as hydrazine or sodium borohydride. The polyol process allows the process to proceed at a first nucleation temperature and a higher growth temperature, substantially separating nucleation and growth of metal nano-clusters and allowing control of the number, mean crystallite size and dispersion of crystallite sizes of nano-clusters.

Applications

Silver-silica particle complexes may have many uses. The cost of production is low enough to allow the complexes to be included in bulk polymers, unlike other sources of ionic silver nanoparticles and silver colloids that are comparatively expensive to produce. In addition, surface coatings, paints, and polymers including silver nanocluster-silica particle complexes are effective in sterilizing surfaces of products or in inhibiting the growth of pathogens, fungus and biofilms on the surface or within crevices or seams of products made with the coatings, paints or polymers. When pathogens contact the surface of the surface coatings, paints or polymers (or are in very near proximity), it is thought that the pathogens are killed by a reactive oxygen species. The silver nano-clusters act on diatomic oxygen molecules to produce reactive oxygen species such as singlet oxygen, ozone or the like. For example, this may result in reactions capable of disrupting respiration of microbes or may damage cell walls.

Figure 11:
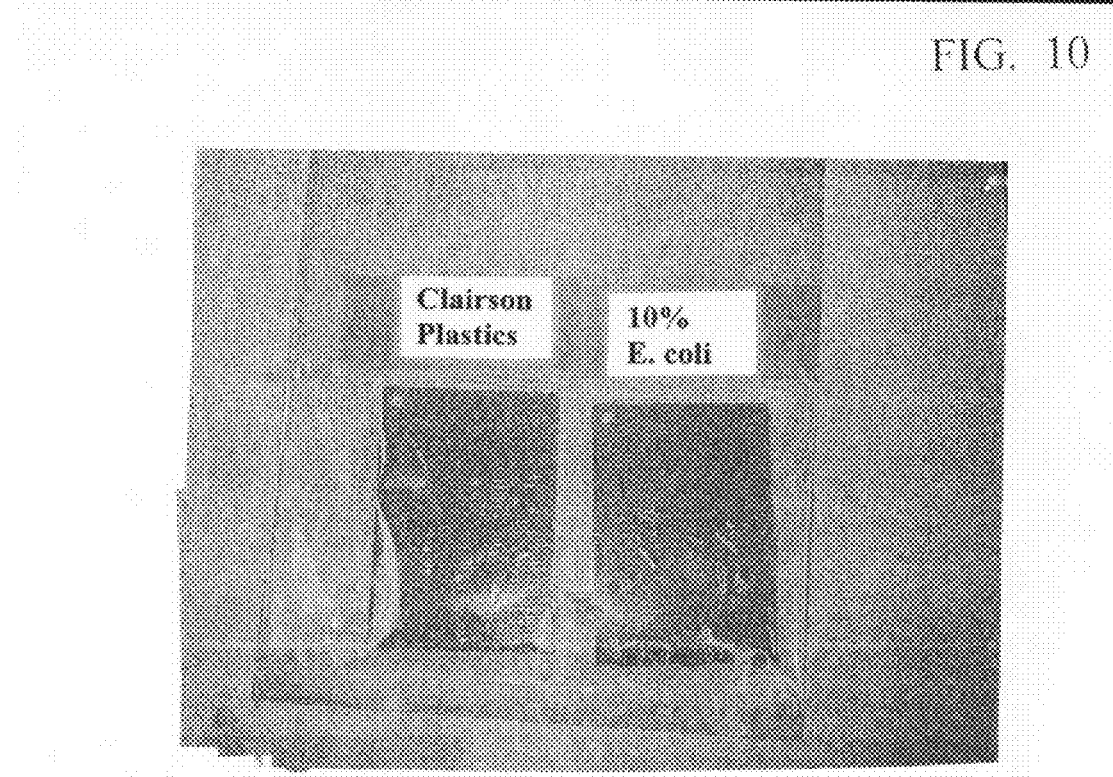
FIG. 11 illustrates two samples, side-by-side, of polyethylene samples with and without silver-silica particles.
Figure 12:
FIG. 12 shows a lab test for a polymer coupon including silver-silica particles confirming no measurable fungus growth.
Figure 13:
FIG. 13 shows a lab test comparing the percent reduction in growth of two different bacteria compared to controls.
Figure 14:
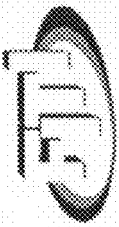
FIG. 14 shows another lab test comparing the percent reduction in growth of two additional bacteria to controls.

For example, FIGS. 11 and 12 are reports showing substantially no fungus growth and a 99.9% reduction in two different types of bacteria, respectively, when placed in contact with the surface of a polymer having silver-silica particles incorporated in the polymer. Another laboratory report shows more than a 90% reduction of *E. coli* in water contained in a vessel containing nano-sized silver-silica particles compared to an untreated container. Testing of residual contamination of liquids exposed to polymers containing up to a 10% let down from a master batch containing silver-silica nano-particles showed no measurable silver (less than 20 parts per billion). In other words, there is no measurable leaching from the polymer. The inventor knows of no other non-leaching antimicrobial exhibiting anywhere near a 90% reduction in bacteria in water within a container over a 3 day period, a 99.9% reduction in bacteria, or the inhibition of fungus growth. Including silver-silica particles in the plastics used in ice machines, water containers, pools, and any other container for liquids is an effective way to reduce *E. coli* in the liquids without introducing any measurable quantity of silver into the liquid. The inclusion of silver-silica particles is effective in preventing growth on the surface of the container, also. Leaching of nanosilver particles and silver ions into liquids and foods is a serious disadvantage for antimicrobial systems using ionic silver, which may prevent adoption of the technology in a wide variety of applications where contact with people, food or liquids raise questions of the safety of migrating silver ions and silver colloids into the people, food or liquids, or even ground water.

A polyol suspension including silver-silica particles may be used directly to produce a product, may be incorporated into a paint or coating material, may be formed into a sheet within a matrix material or may be included in an intermediate product, for example. If included in an intermediate product, such as an extruded master batch, then the master batch may be used to include the silver-silica additive in a polymer in the same way as any other additive would be added using a master batch. Thus, incorporation of the silver-silica particles using a master batch is readily accessible to any person of ordinary skill in the field of polymer extrusion or die injection molding. For example, a master batch may be prepared having a comparatively low concentration of silver-silica nanoparticles with a substantially greater effectiveness as an antimicrobial additive. The concentration of silver in the polymer (only source of silver being the silver-silica particles, for example) after mixing in the master batch pellets with base polymer pellets and extrusion into coupons is measured for three different master batch let downs, as follows:

TABLE 1

| Percent Let Down (master batch:base resin)* | Measured Silver Content mg of silver/kg of polymer (± stdev) |
| --- | --- |
| 0% | 0.00 |
| 2.5% | 0.60 (±0.2) |
| 5.0% | 3.95 (±0.5) |
| 10.0% | 7.00 (±1.28) |

In one method the silver-silica particles are separated and dried. The powder is then mixed with pellets and made into an article of manufacture or a master batch by extrusion. In another example, the silver-silica particles are not dried but are suspended in a liquid. The suspension is mixed as a liquid with a polymer, such as a polymer in the form of a powder, a powdered additive, a pulverized polymer, a granulated polymer or pellets of a polymer. Preferably, a granulated polymer is used that has a grain size large enough to avoid polymer dust becoming airborne but small enough to absorb the liquid suspension without allowing any of the liquid suspension to pool in the bottom of a mixing container. The mixing process may be conducted at a temperature and/or under a vacuum and/or dry air or nitrogen gas to remove some or all of the liquid prior to further processing. In one example, the temperature is at least 40 degrees centigrade. A temperature of at least 80 decrees centigrade will result in a "whitening" of the silver silica particle complexes during the mixing. Tumbling of the mixture during drying is preferred. Drying of the mixture during tumbling prevents out gassing from the liquid during forming of a polymer article, which might produce voids, for example.

In another example, the liquid or powder added to the polymer includes platinum colloid or platinum nano-cluster particle complexes, which are prepared using a polyol process. In the polyol process for platinum nano-cluster particle complexes, the concentration of platinum ions may be reduced by one-tenth compared to a similar process for silver-silica particle complexes. In one example, a platinum colloid is added at 10 wt % of the silver-silica suspension, which is thought to be sufficient to prevent any fouling of the silver nano-clusters over time. In another example, the platinum ions are introduced in a one-pot polyol process.

The effectiveness of test coupons in inhibiting bacterial growth was tested using a testing protocol shown in FIG. 11. Agar, inoculated with a microbe such as *E. coli*, is spread in a layer on a polymer membrane. Then, a plastic coupon is placed in intimate contact on the agar, and the edges of the polymer membrane and agar are carefully trimmed to provide a sample, such as shown in FIG. 11. FIG. 12 shows a pair of samples side by side, each heat sealed in a polymer bag and inserted into another bag for identification. Tests show a very marked inhibition of bacterial, fungal and biofilm growth on a surface treated with silver-silica particle complexes compared to a surface without.

A reduction in *E. coli* of 5% and 10% let down of a master batch formed in to sample coupons show a dramatic reduction in *E. coli* after 24 hours compared to control coupons. At 48 hours, the difference in *E. coli* count is about 2 orders of magnitude less than the control. A let down of 5% appears to be preferred based on the data presented for antimicrobial activity. There is no clear explanation why a higher concentration should not have provided a greater antimicrobial effect, but the data shows that adding almost twice the concentration of silver-silica nanoparticles to the polymer than the 5% let down failed to increase antimicrobial effect. The reduced costs alone are sufficient reason to prefer the 5% let down, even if the 10% let down had not shown a marginally reduced effect. A let down of 2.5% is less effective than either of the higher concentrations but still shows some effectiveness compared to control samples.

Now referring to the antimicrobial assay, in one example ASTM E-2180-01 was used as a "Standard Method for Determining the Activity of Incorporated Antimicrobial Agent(s) in Polymeric or Hydrophobic Materials," utilizing a nutrient agar. About 3.0 grams of agar (Remel 452011) and 0.3 ml of Tween 80 (Sigma Aldrich P-1754) was used to determine the effectiveness of silver-silica particle complexes in protecting polyethylene coupons from a target organism. In one example, the target organism selected was *Escherichia coli* (*E. coli*)-ATCC #5384 (gram negative organism). The test nutrient agar media was prepared and cooled after sterilization. The *E. coli* test organisms were passed through nutrient broth at least twice prior to assay. Approximately 1.0 ml of *E. coli* nutrient growth broth was added and thoroughly mixed into 250 ml of the agar test media. Polyethylene coupons comprising silver-silica particle complexes and without silver added were aseptically placed onto a plastic film inoculated in a linear manner with 1 ml of the agar test media enriched with *E. coli*. Each coupon was placed directly onto the agar bead and allowed to remain in place until the agar had cooled. A sterile scalpel was used to carefully trim the plastic film to the edges of the test plastic coupon. The test coupons are placed into sterile laboratory stomacher sample bags and these bags are heat sealed.

TABLE 2

| | | 24 hours | | 48 hours | |
| --- | --- | --- | --- | --- | --- |
| | | 0.1 ml | 0.1 ml | 0.1 ml | 0.1 ml |
| Coupon Controls | *E. coli* | $1.8 \times 10^8$ | $1.6 \times 10^8$ | $1.4 \times 10^9$ | $1.9 \times 10^9$ |
| | *E. coli* | $1.6 \times 10^8$ | $1.9 \times 10^8$ | $1.1 \times 10^9$ | $1.2 \times 10^9$ |
| Coupon 2.5% | *E. coli* | $6.8 \times 10^7$ | $6.2 \times 10^7$ | $8.4 \times 10^7$ | $8.6 \times 10^7$ |
| | *E. coli* | $6.5 \times 10^7$ | $6.4 \times 10^7$ | $8.6 \times 10^7$ | $8.2 \times 10^7$ |
| Coupon 5.0% | *E. coli* | $7.6 \times 10^6$ | $7.8 \times 10^6$ | $1.8 \times 10^7$ | $1.4 \times 10^7$ |
| | *E. coli* | $7.8 \times 10^6$ | $6.8 \times 10^6$ | $1.2 \times 10^7$ | $1.6 \times 10^7$ |
| Coupon 10.0% | *E. coli* | $8.5 \times 10^6$ | $9.2 \times 10^6$ | $2.8 \times 10^7$ | $2.9 \times 10^7$ |
| | *E. coli* | $9.1 \times 10^6$ | $8.8 \times 10^6$ | $3.2 \times 10^7$ | $3.3 \times 10^7$ |

Figure 17:
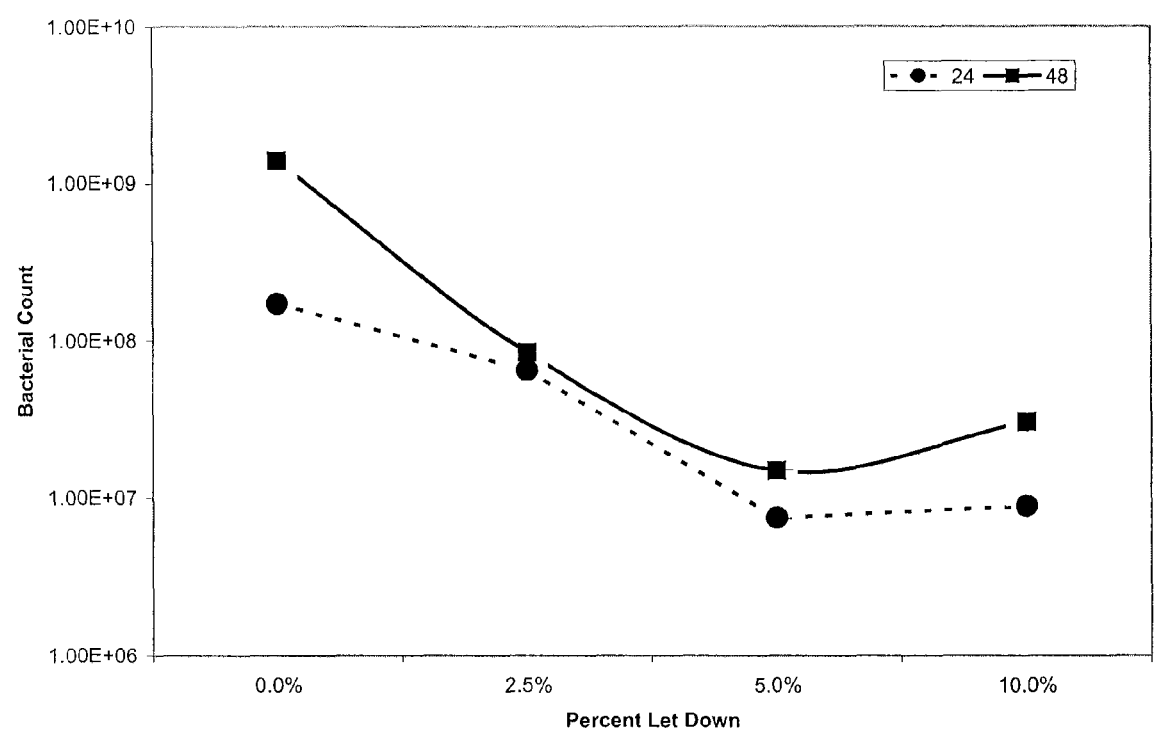
FIG. 17 is a graphical representation of the data in Table 2 at 24 hours (dashed line) and 48 hours (solid line).

The samples were assayed for the microbial levels of growth present at 24 and 48 hours and are reported above in Table 2. Test coupons were assayed by diluting an initial 1:100 volume in sterile phosphate buffer and performing serial dilutions up to $10^6$ for coupons prepared at 2.5%, 5% and 10% master batch let down and up to $10^8$ for control coupons having no silver added. Silver-silica particle complexes, when added to polyethylene test coupons using a master batch additive with let down in a range from 2.5% to 10%, are significantly effective at 24 to 48 Hours in bacterial target kill compared to a control, without any silver additions, under conditions of nutrient availability within a volume in close contact conditions with the test coupons, using an *E. coli* pathogen model, and heat-sealed within a stomacher bag. Interestingly, the results in FIG. 17 are instructive. The control, without any silver, has a dramatic increase in *E. coli* from 24 to 48 hours. Samples prepared with only a 2.5% let down of the master batch have a substantial reduction in *E. coli* compared to the control, but there is not much change from 24 to 48 hours. The amount of bacteria is in stasis. Samples tested at 24 hours for a 5% let down and a 10% let down exhibit similar effectiveness in killing bacteria, both killing more bacteria than the 2.5% let down, but at 48 hours the sample at 5% let down shows a small increase compared to 24 hours and the sample at 10% let down shows a larger increase compared to 24 hours. While at first this might seem counterintuitive, because the presence of silver-silica particle complexes should continue to kill the *E. coli* bacteria, a review of the mechanism for killing *E. coli* bacteria may explain the results. There is no leaching of silver ions or any silver particles from the polymer, as with some other silver ion based antimicrobials. Instead, the silver metal nano-clusters are immobilized on the particle surface. Thus, it is thought that the primary mechanism for killing bacteria is the converting, effectively, of diatomic oxygen to reactive oxygen species that impair bacteria respiration and damage bacteria cell walls, killing the bacteria. This reaction occurs due to the tendency of silver to adsorb and to retain oxygen. However, the test method utilizes stomacher bags to seal the test specimens in a confined space, which prevents much, if any, additional diatomic oxygen from entering the stomacher bag. As a result, the sample at 2.5% let down reaches a stasis at 24 hours and neither increases or decreases its effectiveness at killing bacteria at 48 hours. The more rapid rate of conversion of diatomic oxygen to more reactive species shows an increased kill rate at 24 hours in the sample at a 5% let down; however, the availability of diatomic oxygen and the kill rate both decrease at 48 hours, which allows some small increase in the growth of bacteria. An even more rapid conversion of oxygen to reactive species of the sample with 10% let down depletes diatomic oxygen earlier than the sample at 5% let down, which leads to no improvement over the results of the 5% let down at 24 hours, and a larger increase in the growth of the bacteria at 48 hours. An adequate supply of diatomic oxygen improves the antimicrobial effectiveness of silver nano-clusters. Likewise, a complete lack of oxygen, in one test of polymer including silver-silica nanoparticle complexes, shut down the antimicrobial effect. It is known that oxygen is capable of dissolving in bulk silver at room temperature and dissociates on the various surfaces (110, 111 and 100) with various orientations at various temperatures. Electronic, chemical and thermal adsorption and desorption occurs repeatedly, and it is believed that silver nano-clusters are particularly capable of producing oxygen in more reactive states than its normal diatomic state. However, it is both unexpected and surprising that nano-clusters of silver are capable of producing a sufficient concentration of reactive oxygen species to reduce bacteria by 99.9% or greater, without leaching silver ions and at such low concentrations of silver.

In one example, a supply of oxygen through a polymer package including silica-silver particle complexes is selected such that oxygen is continuously supplied at a level sufficient to activate antimicrobial benefits of silver-silica complexes. Thus, a higher concentration of silver-silica particle complexes requires a correspondingly higher permeability of oxygen. The permeability may be selected by selecting a polymer type having a higher permeability to oxygen, a low density of a polymer or polymer grade having a higher permeability per thickness or a lesser thickness of a polymer barrier material. In one example, a film of polyethylene is formed having a thickness selected in a range from about 1 mil (0.0254 millimeters) to about 3 mils (0.0762 millimeters), with the concentration of silver-silica particle complexes in the 1 mil polyethylene barrier layer being selected to be greater than the concentration of silver-silica particle complexes in the 3 mils polyethylene barrier layer. For example, a polyethylene film of 1.5 mils (0.0381 millimeters) may be selected that has an oxygen permeability of about 10,000 cubic centimeters per square meter in 24 hours and a concentration of silver-silica particle complexes in the polyethylene film in a range from about 5 mg of silver per kilogram of the polyethylene film to about 15 mg of silver per kilogram of the polyethylene film. In another example, a polymer film thickness and permeability are selected having a rate of at least 10,000 cubic centimeters of oxygen per square meter per twenty-four hour period.

Based on the testing results, polymers including silver-silica particles are effective in inhibiting the growth of microbes compared to a control. Unlike some other silver-based antimicrobials, the presence of silver-silica particles and nanoparticles prepared according to the methods provided does not leach into food or liquids in contact with the treated polymer article. This is very surprising and unexpected. All of the other silver-based antimicrobials that are commercially available and effective as antimicrobial additives intentionally leach silver ions. Indeed, their effectiveness depends on leaching and the presence of humidity or liquids in contact with the silver antimicrobial. To our knowledge, there is no other product that has no measurable leaching and still shows effectiveness in inhibiting bacterial growth. In one example, the silver-silica particle complexes are incorporated into at least a surface layer of an extruded or co-extruded polymer fiber, such as a polypropylene or polyester. Initial testing shows that even after 20 wash cycles, a co-extruded polyester having silver-silica particle complexes incorporated in an outer layer of the co-extruded spun fibers resulted in a reduction in bacteria, such as *S. aureus* and *K. pneumoniae*, of 99.9% compared to a control without any silver added. Other antimicrobials, which rely on leaching, suffer from appreciable loss in effectiveness after 20 wash cycles.

It is thought that the binding of the silver clusters to the surface of the silica particles prevents release of silver ions that would otherwise occur in measurable amounts. The mechanism for inhibition of bacterial growth is believed to include the dissociation of diatomic oxygen on the silver metal surface of the high surface area to volume nano-clusters of silver. It is thought that dissociation of diatomic oxygen may be a source of atomic oxygen, singlet oxygen and ozone. It is believed that the very high surface area and adjacent surfaces of nano-clusters of silver on the surface of silica particles, such as shown in FIGS. 2B, 4B and 6B provide an ideal location for production of atomic oxygen, singlet oxygen and ozone. It is further believed that the effects of these chemically reactive forms of oxygen are limited, primarily to the neighborhood nearby the surface of the polymer article or coating containing the silver-silica particles. It is known that chemically reactive forms of oxygen are effective in sanitizing, and ozone is used in laundries, sanitizing fruits and vegetables and the like, without harm to the article being sanitized.

In general, metal-silica or metal-dielectric nanoparticles may be used as catalysts or may be used for their antipathogen and antimicrobial benefits in chemical processes, medical imaging, agricultural fungicides and pesticides and paints or coatings, for example.

In one example, silver-silica polyethylene at a concentration of about 4 mg/kg of silver to polymer, is used as an antifouling coating on a ship hull. The use of the silver-silica containing coating on the ship hull delays the development of a biofilm and makes removal of any biofilm or barnicles much easier. In one example, biomass is merely brushed away without substantial effort compared to a very difficult process of treating or scrubbing on an unprotected surface. In another example, the silver-silica particles are added to the polymer resin in a fiberglass-resin hull or composite hull. In yet another example, the silver-silica particles are added to a coating (marine hull paint) that is applied to a hull.

In one example, silver-silica particles are added to medical devices to prevent or control infection. A mesh for use in surgical repairs includes silver-silica particles, with no measurable leaching of the silver from the mesh. Silver is known to have some adverse effects in humans including turning the flesh blue, at sufficient exposure. Since the mesh is for insertion in a patient and is retained within the patient, it is necessary to show that leaching of silver from the implantable device does not harm the patient. The silver-silica particles do not allow silver to leach from the mesh, but nevertheless reduce the incidence of infection near the surface of the mesh. In another example, a dental prosthesis, such as a crown, an overlay, a cap or a filling material includes silver-silica particles. The dental prosthesis does not leach silver (at least not due to the silver-silica particles). It is believed that the dental prosthesis inhibits microbial growth on the surface of the dental prosthesis. In another example, dental instruments comprise a polymer including silver-silica particles that inhibit microbial growth.

In another example, silver-silica particles are included in implants made of polymers, ceramics and silicone. The implants do not leach silver and prevent microbial growth, sepsis and rejection of the implants by the patient's body. In the example of a ceramic implant or an implant having a ceramic coating, the silver-silica particles are intermixed with the ceramic material and inhibit microbial growth without preventing bone growth or other cellular repair by the patient's body.

In still another example, the medical devices are used externally applied or otherwise external to a patient, but silver-silica is added to inhibit microbial growth. In one example, silver-silica particles are included in the material used to form a cast. The inclusion reduces itching caused by microbial growth between the patient's skin and the inner surface of the cast, without exposing the skin to prolonged contact with leaching silver ions. In yet another example, the silver-silica particles are included in dressings or bandages. In still another example, the silver-silica particles are included in the polymer matrix or resin matrix of medical implements and devices. In yet another example, moldings and surfaces in a hospital are made of a polymer including silver-silica particles to inhibit and kill infectious organisms on such surfaces. Examples of surfaces include light switches, countertops, moldings, work surfaces, sinks, shower surfaces, toilet seats, bed pans, disposable clothing items, masks, glasses, tents, tubing, and any other surface where a non-leaching and antimicrobial material is desirable.

In yet another example, gold nano-clusters are adhered to the surface of dielectric particles, such as polystyrene or silica. The silica or polystyrene particles may be selected to have a mean particle diameter of five to forty nanometers. The gold nano-clusters, which may be reduced from an ionic source of gold in a polyol process, may include clusters of seven gold atoms, for example. Gold clusters having a certain number of gold atoms or a certain size are know to fluoresce upon excitation by an external source of radiation or by other energy transfer mechanisms. Other sizes of gold nano-clusters are known to damp fluorescence of other fluorescent molecules when in close proximity to those molecules by a mechanism of Förster energy transfer. Thus, functionalization of the surface of the dielectric or silica particle may be used to combine the particle, which may be nanoparticles, to other molecules that are known to target certain cells and tissues, such as certain lipids, vitamins, chitans, or the like. Targeting certain cells or certain structures in cells may be used to mark the cells or to treat them. Due to bonding between the gold nano-clusters and the surface of functionalized particles, migration of the gold nano-clusters may be prevented or controlled.

In yet another application, food handling devices, such as bins, cutting boards, packaging products, tier sheets, and pallets may be made of a polymer including silver-silica particles. In this example, the non-leaching of the silver is an important factor in safe use of the food handling and packaging products.

In yet another application, fabrics and textiles include silver-silica or other metal-inorganic particle particles with or without other colloidal nanoparticles. Fabrics including are silver-silica particles may be naturally deodorizing and antimicrobial, for example.

In yet another application, liquid suspensions of silver-silica suspensions may be used as a fungicide to inhibit growth of bacteria, viruses and fungus or other diseases on agricultural crops. Silver-silica may be used to replace copper sulfate and other copper-containing pesticides. Silver-silica or silver nanoparticle suspensions are effective in preventing cucumber mosaic virus and other diseases that are untreatable by any known pesticides, for example. In one example, the particle surface is functionalized to immobilize the particle on a surface or structure of the plant. The immobilized particle having metal nano-clusters, such as silver nano-clusters, immobilized on the surface of the particle acts as a long term fungicide, inhibiting the onset of disease, delaying disease progression or treating diseased plants. In one example, thiol groups that are not bound to silver nano-clusters are used as functional groups for bonding to plants directly or via linking molecules. In one example, a linking molecule is a polymer, a co-polymer, a polysaccharide, or a combination of these. In one example, a polysaccharide is a sugar molecule, such as a fructose or a portion of a fructose polysaccharide, or a cellulose molecule. In another example, the linking molecule is a nitrate or nitrite.

What is claimed is:

1. A one-pot polyol process for making particle complexes, the process comprising:
   synthesizing a plurality of particles in a sol-gel process to form a particle suspension;
   functionalizing the surface of the plurality of particles in the particle suspension, whereby functionalized groups capable of immobilizing silver nano-clusters are formed on the surface of the silica particles;
   adding, without separating the plurality of particles from the particle suspension, a polyol to form a polyol suspension;

mixing a source of metal ions into the polyol suspension;
reducing the metal ions to form a metallic phase; and
nucleating metal nano-clusters on the surface of the plurality of particles functionalized during the step of functionalizing, to form the particle complexes.

2. The process of claim 1, further comprising:
growing a plurality of the metal nano-clusters nucleated during the step of nucleating.

3. The process of claim 2, wherein the step of growing comprises:
increasing the temperature of the polyol suspension; and
maintaining the polyol suspension at a growth temperature in a temperature range, after the step of increasing, for a time period, such that metal nano-clusters grow.

4. The process of claim 3, wherein the step of growing further comprises:
sampling the polyol suspension; and
determining a UV-vis profile for the polyol suspension sampled during the step of sampling.

5. The process of claim 4, wherein the source of metal ions mixed during the step of mixing includes a silver nitrate, and the step of synthesizing includes a silica source such that the plurality of particles include silica particles, and at least of a fraction of the particle complexes include silver nano-clusters disposed on the surface of silica particles.

6. The process of claim 5, further comprising:
introducing a reducing polymer into the polyol suspension such that the reducing polymer is distributed throughout the polyol suspension prior to the step of mixing.

7. The process of claim 6, wherein the reducing polymer is selected to include poly(vinylpyrrolidone).

8. The process of claim 7, wherein the step of mixing provides a concentration of silver ions in a range of 500 ppm to 5000 ppm of the polyol suspension after the poly(vinylpyrrolidone) is distributed throughout the polyol suspension.

9. The process of claim 8, wherein the step of nucleating includes maintaining the temperature at a nucleating temperature of about 25 degrees centigrade for a nucleating period of about 12 hours, repeating the step of sampling at least every hour commencing no later than about 12 hours after the step of mixing, and comparing the profile obtained to a nucleation profile during the step of determining in a process of controlling the nucleation, such that the step of nucleating is terminated based on the step of comparing.

10. The process of claim 9, wherein, upon termination of the step of nucleating, the step of growing is commenced, and after the step of maintaining the polyol suspension at the growth temperature is commenced, repeating the step of sampling at least every thirty minutes, and comparing the profile obtained to a processing profile in a process of controlling the growth, such that the process is terminated based on the processing profile achieving at least a desired peak maximum and a desired width at half maximum, and reducing thereafter the temperature of the polyol suspension.

11. The process of claim 10, further comprising, after the process is terminated, separating at least a portion of the particle complexes from the polyol suspension.

12. The process of claim 11, wherein the process of separating includes diluting the polyol suspension with a diluent to prepare a diluted suspension, and concentrating the particle complexes in a portion of the diluted suspension.

13. The process of claim 12, wherein the process of concentrating the particle complexes includes centrifuging the diluted suspension and removing a portion of the liquid, the portion of the liquid removed including fewer of the particle complexes than the portion of the liquid including concentrated particle complexes.

14. The process of claim 13, wherein the process of separating is repeated at least once.

15. The process of claim 14, wherein the diluent selected for use in the process of separating is different at least one time in the process of separating.

16. The process of claim 13, wherein the step of separating includes drying the particle complexes.

17. The process of claim 1, wherein the step of nucleating includes controlling a nucleating temperature, a concentration of silver ions in the polyol suspension, and the time, such that a plurality of clusters of metal atoms in a range from five to nine atoms are disposed on the surface of a plurality of the particle complexes and are bound to the surface of the particle complexes.

18. A polyol process for making particle complexes, the process comprising:
synthesizing a plurality of particles in a sol-gel process to form a particle suspension;
functionalizing the surface of the plurality of particles in the particle suspension by adding to the particle suspension a mercapto-silane selected from the group of mercapto-silanes consisting of:
a (3-mercaptopropyl)trimethoxysilane having the formula:

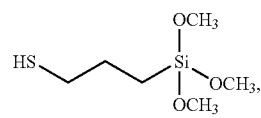

a (3-mercaptopropyl)triethoxysilane having the formula:

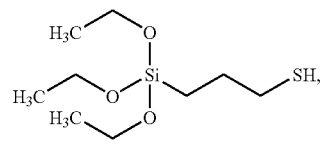

and combinations thereof;
mixing the plurality of particles and a polyol to form a polyol suspension;
mixing a source of metal ions into the polyol suspension;
reducing the metal ions to form a metallic phase; and
nucleating metal nano-clusters on the surface of the plurality of particles functionalized during the step of functionalizing, to form the particle complexes.

19. The process of claim 18, wherein the step of functionalizing selects a (3-mercaptopropyl)triethoxysilane.

20. The process of claim 18, wherein the step of mixing selects ethylene glycol as the polyol.

21. The process of claim 20, wherein the step of mixing includes adding a poly(vinylpyrrolidone) to the polyol suspension as a reduction agent and as a control additive in the step of reducing and mixing of the poly(vinylpyrrolidone) and the step of mixing includes using a stirring mechanism that gently mixes the poly(vinylpyrrolidone) in the polyol suspension without breaking a substantial number of the poly (vinylpyrrolidone) polymer chains.

22. The process of claim 21, wherein substantially all of the poly(vinylpyrrolidone) is dissolved prior to the step of mixing a source of metal ions into the polyol suspension.

23. A process of preparing a non-leaching antimicrobial additive comprising the process of claim 18, wherein the source of metal ions added during the step of mixing includes a source of silver ions and further comprising:

mixing a polymer precursor or polymer material with the suspension at a temperature of at least forty degrees centigrade, such that the suspension is mixed with the polymer precursor or polymer material to form a mixture; and forming the mixture, such that a mean concentration of silver in the mixture, after the forming process, is in a range from five milligrams of silver per kilogram of the mixture to one hundred fifty milligrams of silver per kilogram of the mixture.

24. The process of claim 23, wherein the mean concentration of silver in the mixture is at least fifty milligrams of silver per kilogram of the mixture.

* * * * *